US008238649B2

(12) United States Patent
Stanton et al.

(10) Patent No.: US 8,238,649 B2
(45) Date of Patent: Aug. 7, 2012

(54) METHODS AND APPARATUS FOR DISPLAYING IMAGES

(75) Inventors: Martin Stanton, Concord, MA (US); Alexander Stewart, Waltham, MA (US); Edward Bullard, London (GB)

(73) Assignee: Dexela Limited, London (GB)

( * ) Notice: Subject to any disclaimer, the term of this patent is extended or adjusted under 35 U.S.C. 154(b) by 0 days.

(21) Appl. No.: 12/842,480

(22) Filed: Jul. 23, 2010

(65) Prior Publication Data
US 2011/0012897 A1    Jan. 20, 2011

Related U.S. Application Data

(63) Continuation of application No. 11/603,844, filed on Nov. 22, 2006, now abandoned, which is a continuation-in-part of application No. 11/595,664, filed on Nov. 9, 2006, now Pat. No. 7,545,907.

(60) Provisional application No. 60/735,140, filed on Nov. 9, 2005.

(51) Int. Cl.
*G06K 9/00* (2006.01)
*G06K 9/40* (2006.01)
*A61B 6/00* (2006.01)

(52) U.S. Cl. ............ 382/154; 382/132; 382/254; 378/4; 600/443

(58) Field of Classification Search ............... 382/154, 382/173, 181, 190, 201, 228, 276, 285, 128–133, 382/254; 600/443; 250/208.1; 348/E5.037, 348/E5.091, E5.079, E3.018, 303; 257/E31.057, 257/E29.23, E31.054, 233, E27.154; 430/311; 424/9.3; 378/37, 97, 108–112, 4, 95–96
See application file for complete search history.

(56) References Cited

U.S. PATENT DOCUMENTS

| 5,949,811 | A  | * | 9/1999  | Baba et al. ............... 378/108 |
| 6,744,848 | B2 |   | 6/2004  | Stanton et al. |
| 7,123,684 | B2 | * | 10/2006 | Jing et al. .................. 378/37 |
| 7,545,907 | B2 |   | 6/2009  | Stewart et al. |
| 7,570,732 | B2 |   | 8/2009  | Stanton et al. |
| 2001/0038681 | A1 | * | 11/2001 | Stanton et al. ............ 378/55 |
| 2003/0095624 | A1 |   | 5/2003  | Eberhard et al. |

(Continued)

OTHER PUBLICATIONS

B. Li, G. B. Avinash, R. Uppaluri, J. W. Eberhard, B. E. H. Claus, "The impact of acquisition angular range on the z-resolution of radiographic tomosynthesis," International Congress Series, 2004, pp. 13-18.

(Continued)

*Primary Examiner* — Sheela Chawan
(74) *Attorney, Agent, or Firm* — Wolf, Greenfield & Sacks, P.C.

(57) ABSTRACT

In one aspect, a method of displaying data is provided. The method comprises obtaining projection data of an object by exposing an object to radiation at a plurality of view angles and detecting at least some of the radiation exiting the object to form the projection data, operating a computer to reconstruct the projection data at a reconstruction resolution to form image data comprising a plurality of voxels representing locations within the object, each of the plurality of voxels being assigned an associated intensity indicative of a density of the subject matter at the respective location, determining a maximum resolution for display, above which variation in intensity between adjacent voxels is not supported by information in the projection data, the maximum resolution being less than the reconstruction resolution, and displaying the image data at or below the maximum resolution.

6 Claims, 19 Drawing Sheets

U.S. PATENT DOCUMENTS

2005/0113681 A1    5/2005   DeFreitas et al.
2005/0226375 A1   10/2005   Eberhard et al.

OTHER PUBLICATIONS

W. A. Kalender, "Computer-tomographie," Grundlagen, Geratetechnologie, Bildqualitat, Anwendungen, Computer-tomographie, Jun. 1, 2006, pp. 112-114.

T. Wu, A. Stewart, M. Stanton, T. McCauley, W. Philllips, D. B. Kopans, R. H. Moore, J. W. Eberhard, B. Opsahl-Ong, L. Niklason and M. B. Williams, "Tomographic mammography using a limited number of low-dose cone-beam projection images," Med. Phys., Mar. 2003, pp. 365-380, vol. 30, No. 3.

International Search Report for International application No. PCT/US2007/024161 mailed Jun. 16, 2008.

* cited by examiner

METHODS AND APPARATUS FOR DISPLAYING IMAGES

RELATED APPLICATIONS

This application is a continuation (CON) of U.S. application Ser. No. 11/603,844 entitled "METHODS AND APPARATUS FOR DISPLAYING IMAGES," filed Nov. 22, 2006, which is a continuation-in-part (CIP) of U.S. application Ser. No. 11/595,664 entitled "METHODS AND APPARATUS FOR OBTAINING LOW-DOSE IMAGING," filed Nov. 9, 2006, which claims priority under 35 U.S.C. §119(e) to U.S. Provisional Application Ser. No. 60/735,140, entitled "PLANAR IMAGING METHODS AND TECHNIQUES," filed on Nov. 9, 2005, each of which is herein incorporated by reference in its entirety.

FIELD OF THE INVENTION

The present invention relates to radiation imaging, and more particularly, to displaying image data reconstructed from projection data of an object obtained from a plurality of view angles.

BACKGROUND OF INVENTION

Imaging apparatus that utilize relatively high energy radiation such as x-ray and gamma rays are widely used to obtain images of subject matter more or less opaque to electromagnetic energy in the visual spectrum. For example, x-ray imaging technology has been employed in a wide range of applications from medical imaging to detection of unauthorized objects or materials in baggage, cargo or other containers. X-ray imaging typically includes passing high energy radiation (i.e., x-rays) through an object to be imaged. X-rays from a source passing through the object interact with the internal structures of the object and are altered according to various characteristics of the material (e.g., transmission, scattering and diffraction characteristics, etc.) which the x-rays encounter. By measuring changes in the x-ray radiation (e.g., attenuation, modifications to the energy spectrum, scatter angle, etc.) that exits the object, information related to characteristics of the material, such as the density distribution, may be obtained.

Computer tomography (CT) techniques involve capturing transmitted x-ray information from numerous angles about an object being imaged to reconstruct a three-dimensional (3D) volume image of the object. The data obtained from each view angle is referred to as projection data or view data and is indicative of the absorption characteristics of the object in directions related to the respective view angle. CT imaging often involves obtaining hundreds or thousands of projections to form a 3D reconstruction of the projection data, thus requiring the object to be exposed to relatively large doses of x-ray radiation and/or to (large or small) doses of radiation over relatively long exposure times. Such large doses and/or imaging times may not be suitable for certain imaging applications having particular safety and/or time constraints. For example, when imaging human tissue, and/or when the imaging procedure is performed on a routine or frequent basis (such as is often the case in mammography), dose levels and/or exposure times used in conventional CT imaging may exceed that which is more desirable.

To reduce a patient's exposure during breast imaging procedures (e.g., imaging of the human female breast), conventional mammography is often performed by obtaining only a pair of two-dimensional (2D) radiographic images of the breast (i.e., each image is reconstructed from a single projection of the breast), typically acquired at approximately complementary angles to one another. However, the superposition of structure within the breast that occurs when 3D structure is projected onto two dimensions often obscures the true nature of the structure. This superposition of structure may make it difficult to identify or detect tissue anomalies. For example, distinct structure in 3D that overlaps in 2D may make it difficult to distinguish cancerous subject matter from benign subject matter within the breast.

Thus, conventional approaches to providing generally low-dose radiation imaging suffer from images that provide confusing representations of internal structures of an object due, at least in part, to the projection of three-dimensional structure onto one or more two-dimensional images. The resulting superposition of distinct structure located at different levels in 3D makes discerning the actual structure in a 2D representation difficult, rendering conventional imaging procedures vulnerable to errors in diagnosis. In mammography, the inability to ascertain the true nature of breast structure may result in both significant false negative and false positive rates, leading to potential missed early stage cancers in the case of the former, or unnecessary trauma to the patient and/or unnecessary hospital visits, surgical procedures, etc., in the case of the latter.

To address such problems, it has been proposed to use a selected number of projections obtained from a plurality of view angles to reconstruct a 3D image, while still respecting a relatively low dose budget (e.g., dose budgets suitable for mammography or other tissue exposures that are generally dose limited due to safety concerns). U.S. Pat. No. 6,744,848 (hereinafter the '848 patent), entitled "METHOD AND SYSTEM FOR LOW-DOSE THREE-DIMENSIONAL IMAGING OF A SCENE," describes various methods and apparatus for obtaining 3D images in a relatively low dose environment. In addition, U.S. Pat. No. 5,872,828 (hereinafter the '828 patent), entitled "TOMOSYNTHESIS SYSTEM FOR BREAST IMAGING," describes various methods of reconstructing projection data from a generally limited number of view angles to form a 3D image. Both the '848 and '828 patents are herein incorporated by reference in their entireties.

DETAILED DESCRIPTION

Figure 1:
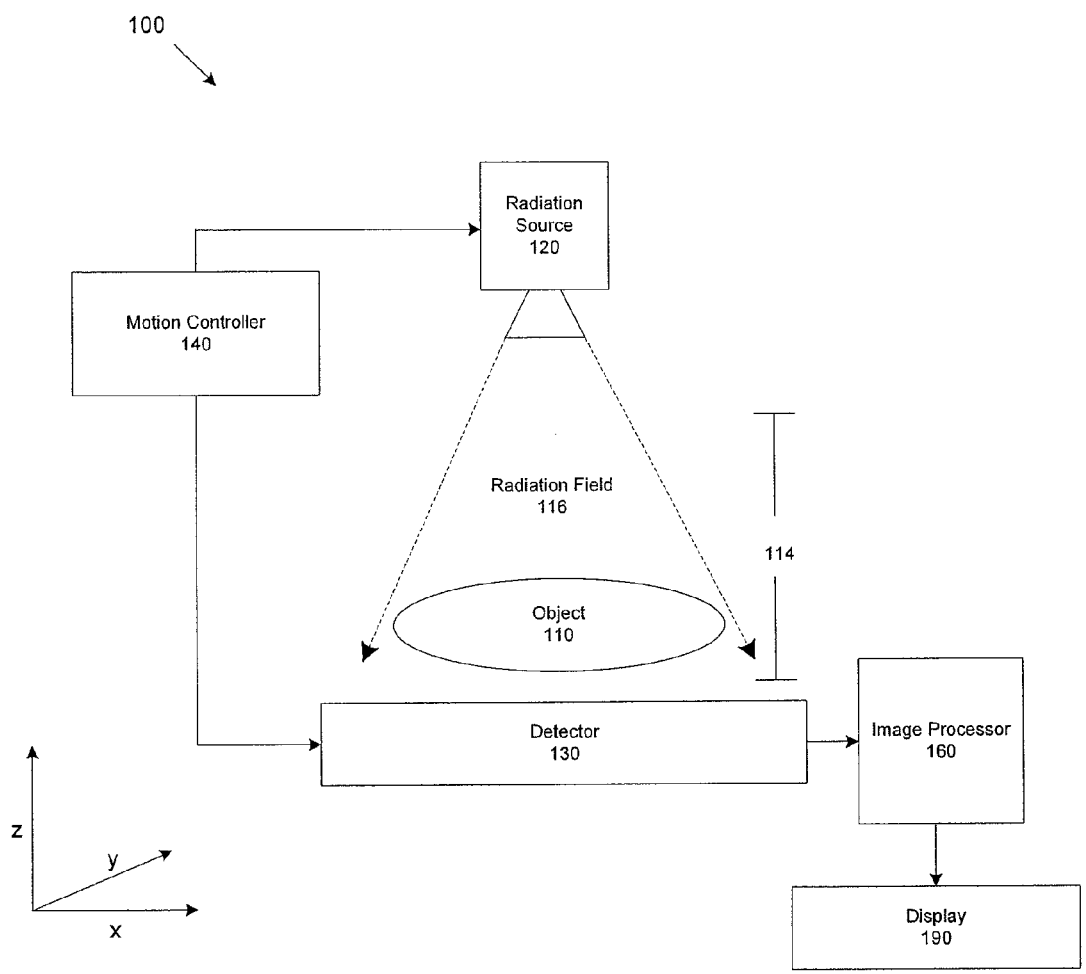
FIG. 1 is a diagram of an imaging apparatus suitable for implementing various aspects of the present invention.

As discussed above, problems of conventional low-dose imaging associated with the projection of three-dimensional structure onto one or more two-dimensional images, have been addressed by obtaining projection data at a relatively limited number of view angles to reconstruct a 3D image of an object exposed to radiation. For example, the '828 and '848 patents described various methods of obtaining projection data of an object in relatively low dose environments, and reconstructing the projection data to form a 3D image of the object. Because the reconstructed image is in 3D, the structure of the object at different depths may not be superimposed on top of one another in a confusing representation (at least not to the same degree as in radiographic images).

An operator (e.g., a radiologist or other diagnostician) may be able to view the 3D image at different depths to analyze the respective structure present there. Such a capability may significantly improve the operator's ability to distinguish structure, for example, to differentiate healthy tissue from anomalous tissue such as a tumor. In particular, an operator can navigate about the image to examine desired portions of the object without having structure from other depths interfering with the analysis. In this way, 3D images may assist in increasing the diagnostic quality of the images.

However, in some circumstances, 3D images are displayed in such a way as to be misleading, potentially (and unintentionally) leading to misdiagnosis. In particular, conventional display methods may provide image data at a resolution higher than the resolution of the information available in the projection data. For example, certain high frequency information not available in the projection data may be presented in the image data as an artifact of the reconstruction data. Thus, voxel-to-voxel (or pixel-to-pixel) changes in density values represented at higher resolution than the projection data may therefore be artificial and not attributable to structure of the object.

Radiologists may perceive these changes, and may improperly characterize the changes as resulting from anomalous subject matter. For example, in breast imaging, a radiologist may characterize these changes as resulting from micro-calcifications, early stage tumor and/or other anomalous tissue that may be indicative of cancer. Accordingly, displaying 3D images at resolutions that are higher than supported by the projection data may actually increase rates of misdiagnosis by allowing the physician to, in a sense, over-interpret the image data. That is, if image data is displayed at too high a resolution, a radiologist may interpret artifacts as variation due to actual structural features of the object.

Applicant has appreciated that by limiting the display resolution of image data, changes in density values not reflective of the projection data (i.e., artifacts) may be suppressed (i.e., not displayed) to avoid the artifacts being interpreted as structure. In some embodiments, image data is displayed at a resolution less than the resolution at which it was reconstructed. For example, the display resolution may be the same or substantially the same as the actual resolution of the acquired projection data. As a result, artifacts in the reconstructed image data resulting from the artificially high reconstruction resolution may be suppressed to avoid the artifacts from being displayed, and potentially mis-interpreted.

There are many instances in which it may be desirable to display image data at a resolution less than the resolution at which it was reconstructed. For example, in some circumstances, the monitor, screen or other output device used to display image data may not have the capability of displaying the image data at full resolution. In addition, for displays with high resolution capabilities, it may be desirable to display more than one image simultaneously such that the display can only accommodate the multiple images at reduced resolutions. As discussed above, Applicant has also appreciated that it may be beneficial to display image data at lower resolutions even if the display capabilities are sufficient to avoid displaying artifacts of the reconstruction algorithm.

Conventional techniques used in reducing display resolution tend to have deleterious effects on the image. For example, various averaging techniques may blur the image, removing high frequency information that may be important in the analysis of the image. For example, in medical imaging, high frequency information is often associated with anomalous tissue that is the subject of the diagnosis. In breast imaging, micro-calcifications, early stage tumors, etc., are often characterized by relatively high frequency and/or high contrast information. Accordingly, conventional approaches to reducing display resolution may obscure the very subject matter for which the images are being obtained.

Applicant has identified various techniques for reducing the resolution of image data for display that may maintain increased image fidelity over conventional techniques. In particular, Applicant has identified techniques for reducing the resolution that obscure less of the salient, high frequency and/or high contrast information. In some embodiments, a maximum intensity value of a neighborhood of pixels is used as the representative pixel intensity for the neighborhood. In some embodiments, a root mean square value of a neighborhood of pixels is used as the representative pixel intensity for the neighborhood. In some embodiments, a function is performed on the pixel intensities of a neighborhood, followed by one or more operations to determine a single pixel intensity for the neighborhood. The inverse of the function may then be applied to the single pixel intensity to form the representative pixel intensity for the neighborhood.

As discussed above, 3D images may assist in remedying confusing representations that occur when structure at different depths are superimposed on one another. To further assist in accurate inspection of medical images, Applicant has developed a process, implemented (for example) in software executing on a computer, that allows an operator to navigate through a 3D image, for example, by allowing an operator to control the depth at which the image is displayed. In conventional navigation controls, structure at different depths may appear and disappear abruptly as the operator progresses from one depth to another, resulting in a very unintuitive experience for the operator that may lead to incorrect diagnosis. Applicant has developed methods of displaying information such that depth transitions appear more natural and intuitive.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments below may be used alone or in any combination, and are not limited to the combinations explicitly described herein.

As discussed above, conventional CT imaging may be employed to obtain 3D images of an object. However, full CT imaging requires subjecting an object to hundreds or even thousands of exposures. Accordingly, CT imaging may be unsuitable for imaging human tissue, and/or performing regular or frequent imaging procedures on human subjects (e.g., breast imaging). The '848 patent describes various methods of obtaining 3D images, while limiting the exposure to radiation dose levels suitable for imaging human tissue.

FIG. 1 illustrates one embodiment of an imaging system 100 suitable for obtaining projection data suitable for forming 3D images in a relatively low-dose environment, in accordance with various aspects of the present invention. Imaging system 100 may be suitable for obtaining projection data and reconstructing images according to the various methods described in the '848 patent and/or the '664 application.

Imaging system 100 includes a radiation source 120, a detector 130, a motion controller 140, an image processor 160 and a display 190. The imaging system 100 can be used to image a single object 110 or a plurality of objects located within an exposure area 114. The exposure area 114 defines generally the region of space between the radiation source 120 and the detector 130, and is located in the path of the radiation provided by radiation source 120 in the direction of detector 130. The exposure area 114 may be the entire region of space located in the path of the radiation passing from the radiation source 120 to the detector 130, or only a predetermined portion of the space.

Radiation source 120 may be any component or combination of components capable of emitting radiation such as x-ray or gamma radiation. In imaging system 100, radiation source 120 is positioned to emit radiation toward exposure area 114 such that, when object 110 is present in exposure area 114, at least some of the radiation impinges on object 110. In particular, the radiation source 120 is adapted to emit radiation to form a radiation field 116, which may be of any shape or size. In a preferred embodiment, radiation field 116 is a beam that radiates outward from a focal point of radiation source 120 substantially in the shape of a cone, that substantially encloses object 110 within a cone of x-rays during exposures. However, radiation field 116 may form other shapes such as a fan beam, pencil beam, etc., and may be arranged to expose any portion of object 110, as the aspects of the invention are not limited in this respect.

Radiation source 120 may be capable of being moved about object 110 such that radiation may be directed at object 110 from a plurality of angular positions, i.e., a plurality of view angles with respect to object 110 (e.g., as described in further detail below). Detector 130 is positioned to receive at least some of the radiation that passes through the exposure area 114, and in particular, radiation that has penetrated and exited object 110. Detector 130 may be a single detector, or a detector array disposed continuously or at a plurality of discrete locations. Detector 130 may be formed from any type of material responsive to radiation generated by radiation source 120. In response to impinging radiation, detector 130 produces signals indicative of the intensity of radiation impinging on the detector surface. Accordingly, recorded intensities of radiation passing through the object as represented by the detector signals carry information about the absorption characteristics of object 110, and form, at least in part, projection data of object 110.

Detector 130 may be configured to be moved in correspondence with the radiation source 120 to detect radiation exiting object 110 from the plurality of view angles. Motion controller 140 may be coupled to radiation source 120 and detector 130 to cause the rotational movement of the radiation source/detector apparatus such that, as the apparatus rotates about the object, the object remains positioned within the exposure area between the source and detector. Motion controller 140 may be capable of being programmed to move the radiation source and detector to any desired view angle with respect to object 110. Together, the radiation source 120, detector 130 and motion controller 140 permit projection data of object 110 to be obtained from any set of view angles. In some embodiments, motion controller 140 may be programmed to control the position of the radiation source and detector independently. For example, the motion controller may move the radiation source and detector along different paths as projection data is obtained from the different view angles, as the aspects of the invention are not limited in this respect.

In another embodiment, the detector 130 remains stationary as the radiation source is moved about the object. For example, if the detector 130 is sufficiently large (e.g., a flat panel two-dimensional detector array) and/or if the angular range over which projection data is obtained is sufficiently small (e.g., the angular range is limited to a range between 5° and 45° both clockwise and counterclockwise from a reference view angle), a single position for the detector 130 may be sufficient to capture projection data from each of the desired view angles. In addition, in embodiments where detector 130 remains stationary, the object may be positioned in direct contact with the detector.

At each orientation, referred to as a view angle, the detector signal generated by each detector in the array indicates the net total absorption (i.e., attenuation) incurred by material substantially in a line between the radiation source and the detector. Therefore, the array of detection signals at each view angle records the projection of the object onto the detector array at the associated view angle. For example, using a 2D detector array, the resulting detector signals represent the 2D density projection of the object on the detector array at the corresponding view angle. The signals generated by the detectors form, at least in part, projection data (or view data) of the object.

Projection data obtained from multiple view angles about the object may be used to compute a density distribution of the object (i.e., to determine density values for locations within the object). The process of converting projection data (i.e., attenuation or transmission as a function of view angle) to density data (i.e., density as a function of location within the object) is referred to as reconstruction. That is, density values are reconstructed from information contained in the projection data. Typically, density values are expressed as image data, i.e., pixel or voxel intensities in two-dimensional (2D) and three-dimensional (3D) images, respectively.

Image processor 160 may be configured to reconstruct the projection data to form images of the object (e.g., 2D or 3D images of the object). Image processor 160 may be configured to implement any desired reconstruction algorithm capable of mapping recorded radiation intensity values (e.g., detector signals from detector 130) to corresponding density values at a desired resolution. Image processor 160 may also be configured to automatically process reconstructed images to, for example, reduce the resolution of the image data for display, transform reconstructed image data to display image data to facilitate image navigation, etc., as described in further detail below. It should be appreciated that image processor 160 may be configured to carry out any computation and/or combination of computations described herein, as the aspects of the invention are not limited in this respect.

Image processor may be one or more processors located proximate or remote from the radiation source and detector. The image processor may be configured to execute programs stored on a computer readable medium such as a memory, accessible by the image processor. Image processor may be part of a computer or computer system capable of receiving projection data. Imaging system 100 may also include a display 190, such as a monitor, screen and/or other display device capable of presenting a pixel representation of reconstructed image data (e.g., display image data). It should be appreciated that the above described components are merely exemplary, and any suitable imaging apparatus of any configuration and/or combination of components may be used to implement any one or combination of the methods described above, as the aspects of the invention are not limited in this respect.

Figure 2A:
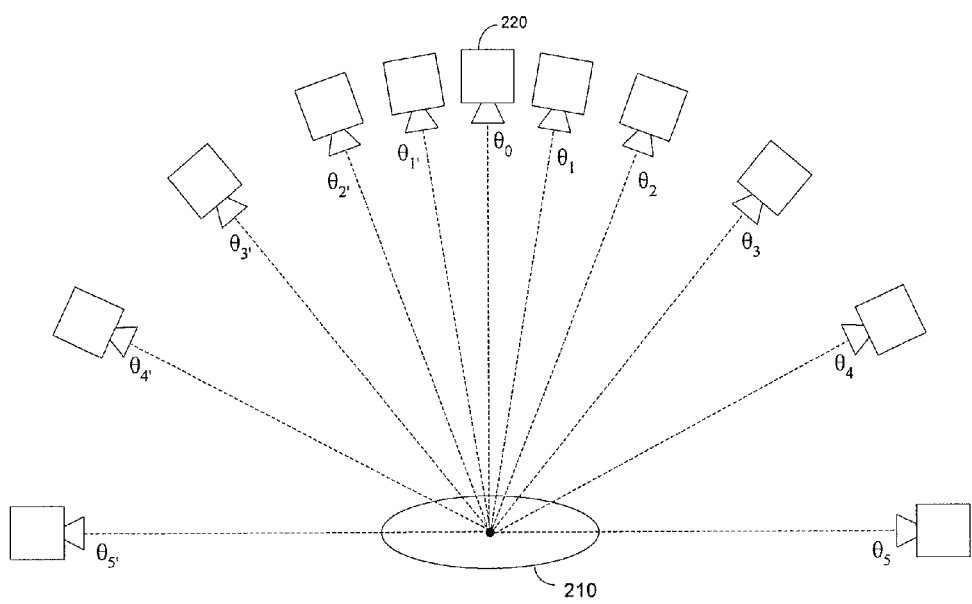
FIGS. 2A and 2B are diagrammatic illustrations of respective exemplary view angle configurations, in accordance with embodiments of the present invention.
Figure 2B:
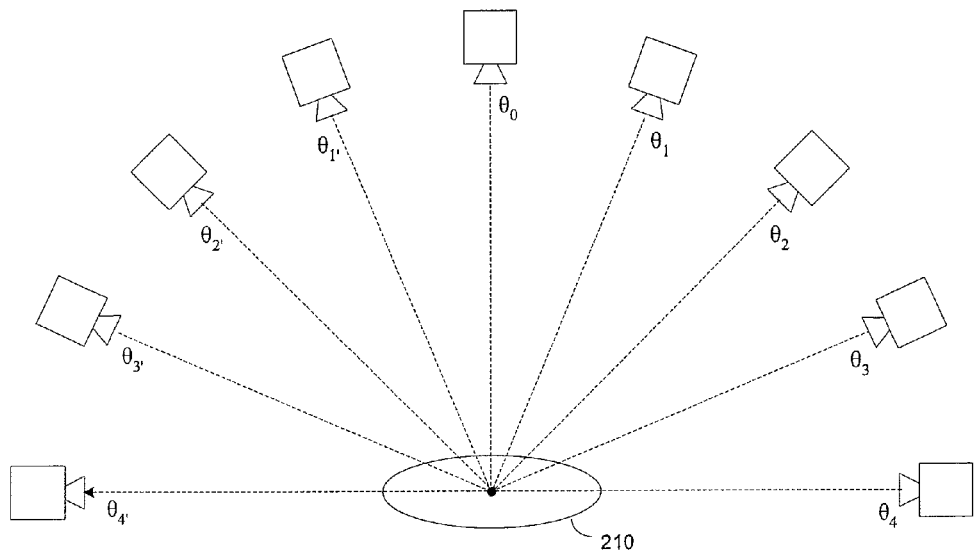

Projection data may be obtained in many different ways. As discussed in the '848 patent, radiation exposures may be performed at a number of non-uniformly distributed view angles. For example, the change in angle from one view angle to another may increase as the angle from a reference view angle (e.g., position A in FIG. 1) increases. That is, as a radiation source is rotated about an object from a reference position, the angle between successive exposures may be increased. However, the various view angles selected also may be uniformly distributed, as the aspects of the invention are not limited in this respect. FIGS. 2A and 2B illustrate exemplary methods of obtaining projection data of an object from a plurality of view angles.

In FIG. 2A, the plurality of view angles used to obtain projection data of object 210 are distributed with non-uniform angular offsets with respect to one another. For example, as the view angles are rotated away from a reference view angle at $\theta_0=0°$ in both the clockwise and counterclockwise directions, the angle between each successive view angle increases. In particular, in the clockwise direction $(\theta_1-\theta_0) < (\theta_2-\theta_1) < (\theta_3-\theta_2)$, etc. Similarly, in the counterclockwise direction, $(\theta_{1'}-\theta_0) < (\theta_{2'}-\theta_{1'}) < (\theta_{3'}-\theta_{2'})$. As discussed in the '848 patent, performing exposures at non-uniform angles may facilitate obtaining optimal projection data for a given dose budget. It should be appreciated that the number and distribution illustrated in FIG. 2A are merely exemplary.

Any number of view angles may be used at any desired distribution, as the aspects of the invention are not limited in this respect. Moreover, the view angles need not be distributed symmetrically with respect to the reference view angle, as any desired distribution may be used with the various aspects of the invention. Furthermore, the total angular range of the view angles at which projection data is obtained need not be equal to 180°, but may cover any desired range. For example, the angular range could cover as little 5° or less or could be any range up to and including 360°.

Figure 3A:
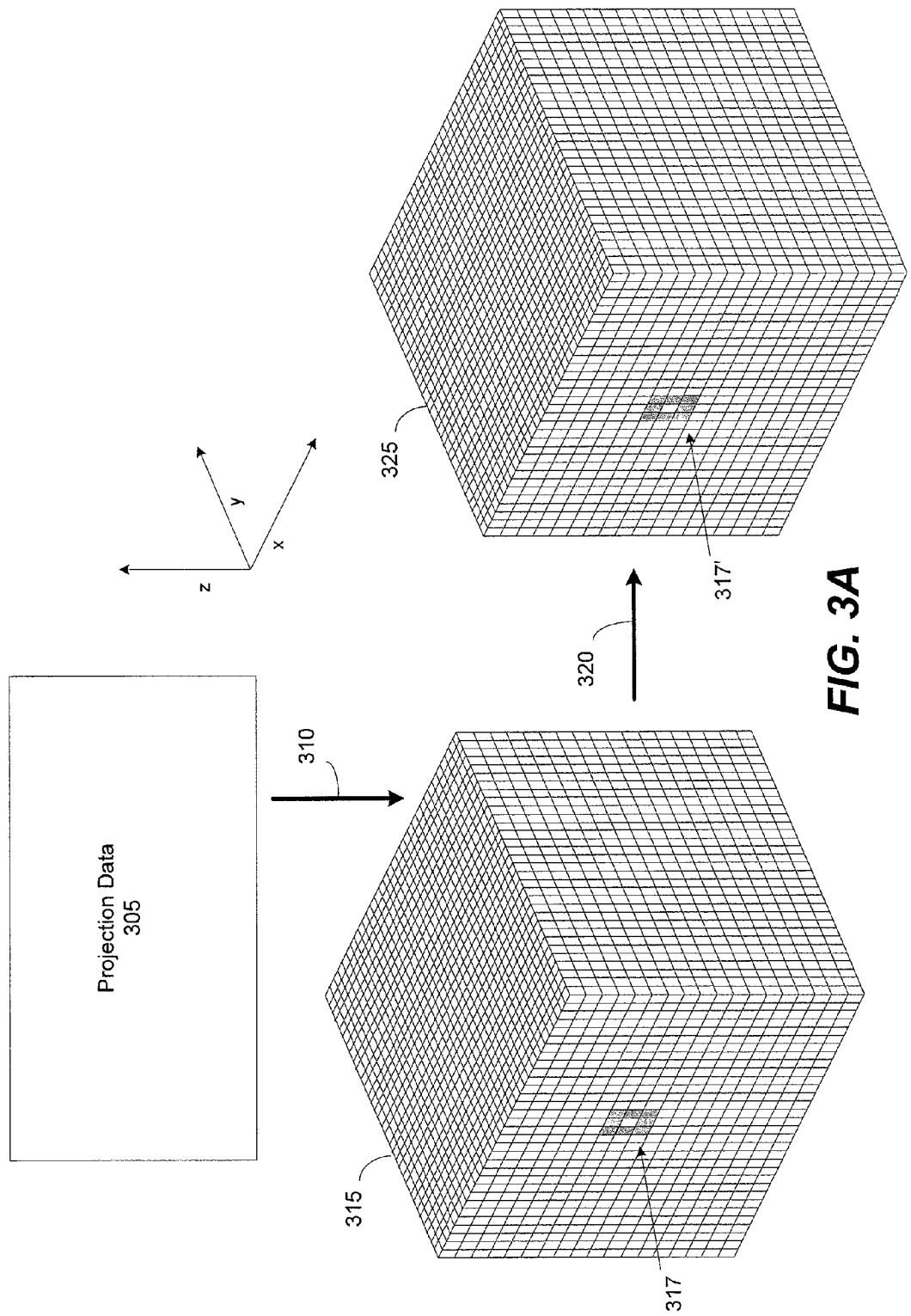
FIG. 3A is a diagram illustrating displaying image data at the same resolution at which it was reconstructed.
Figure 3B:
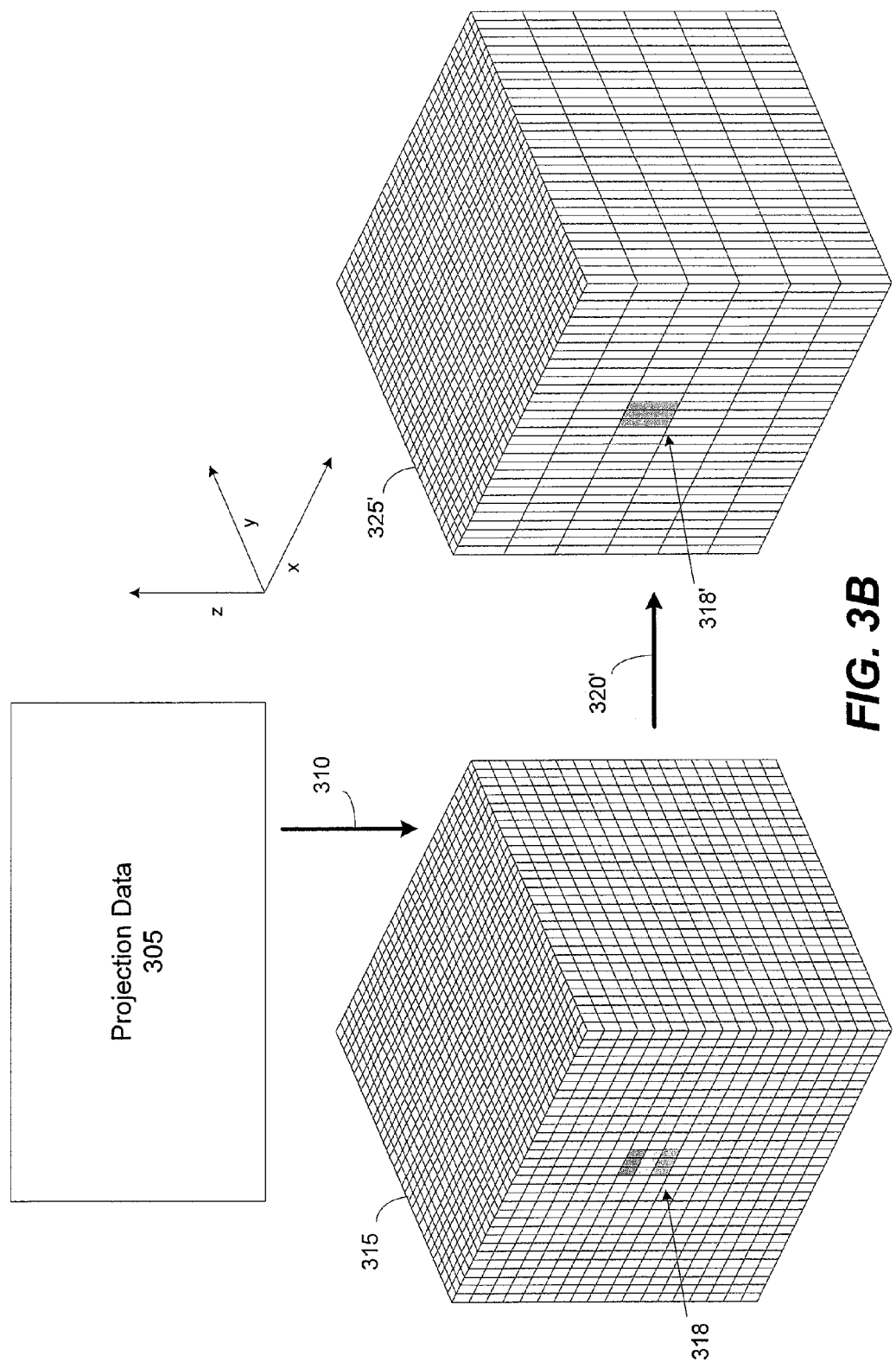
FIG. 3B is a diagram illustrating displaying image data at a lower resolution than which it was reconstructed, in accordance with some embodiments of the present invention.

In FIG. 2B, the angular offsets are distributed essentially uniformly about object 210. For example, as the view angles are rotated away from the reference view angle at $\theta_0=0°$ in both the clockwise and counterclockwise directions, the angle between each successive view angle remains essentially the same. In particular, in the clockwise direction, $(\theta_1-\theta_0)=(\theta_2-\theta_1)=(\theta_3-\theta_2)$, etc. Similarly, in the counterclockwise direction, $(\theta_{1'}-\theta_0)=(\theta_{2'}-\theta_{1'})=(\theta_{3'}-\theta_{2'})$. Accordingly, any number of view angles may be distributed in any fashion; uniformly or non-uniformly, symmetric or asymmetric, etc., as the aspects of the invention are not limited in this respect. As discussed above, the angular range over which projection data is obtained need not be 180° as illustrated in FIGS. 3A and 3B, but may cover a range greater than or less than 180°, as discussed in further detail below.

Projection data obtained according to the methods described above may have different resolutions along the different axes (i.e., asymmetric resolution). In particular, because projection data is obtained at fewer view angles than in full CT (e.g., between 15-50 view angles versus hundreds or even thousands of view angles), the resolution in the z-direction (see e.g., the coordinate frame in FIG. 1) may be substantially less than in the x-direction and y-direction. That is, because less information is available along the z-axis, reconstruction may be unable to accurately assign density values at the same resolution achievable in the XY plane (also referred to as the in-plane).

The resolution in the x-direction and y-direction may be largely a function of the resolution of the detector array and the operating parameters of the radiation source. For example, each detector or detector location capable of being sampled for a detection signal may correspond to a pixel in the resulting image (e.g., a pixel in a slice of a 3D image through the XY plane). In addition, the resolution in the XY plane may also be a function of the radiation intensity, radiation energy and/or radiation field density of the radiation emitted from the radiation source. The resolution in the XY plane is substantially independent of the number of view angles from which projection data is obtained.

However, each pixel in the z-direction is determined from tomosynthetically computing information from projection data obtained from multiple view angles. As a result, the resolution in the z-direction (also referred to as the out-of-plane direction) may be increased by obtaining projection data from an increasing number of view angles. That is, increasing the angular range and decreasing the spacing between successive view angles at which projection data is obtained each contribute to the resolution in the z-direction. However, as discussed above, the greater number of view angles at which projection data is obtained, the greater the exposure of the object to radiation and the longer the acquisition time. Some imaging applications may be limited to a particular radiation dose-budget guided by safety and/or time constraints, thereby limiting the number of view angles at which projection data should be obtained. As a result, in many applications, the in-plane resolution will be greater than the out-of-plane resolution.

As discussed above, reconstruction involves transforming projection data (e.g., attenuation information as a function of view angle) into image data (e.g., density values as a function of location). While there are many different methods of performing reconstruction, the methods perform the same fundamental operation of mapping intensity values recorded at the detectors to density values at discrete locations in space (e.g., mapping detector signals to values in an image that represent 2D or 3D space). The reconstruction algorithm may be configured to map values to a space partitioned into volumes of any size, which may be the same or different than the actual resolution of the projection data from which the image data is determined.

The actual resolution relates to the amount of information in the projection data. The reconstruction resolution relates to how finely space is partitioned for reconstruction (i.e., how small are the logical volumes representing discretized space, each of which are assigned a density value). The display resolution refers to the resolution at which image data is displayed on, for example, a monitor, screen or other display device. Projection data is often reconstructed at a resolution higher than the information available in the projection data (i.e., the reconstruction resolution is greater than the actual resolution).

In some instances, reconstructing at higher resolutions than the actual resolution may be necessary to account appropriately for the geometry of the acquisition process. As a result, at least some of the information in the image data is artificial (e.g., it has no physical basis in the projection data and is therefore an artifact of the reconstruction process). Conventionally, image data is displayed at the reconstruction resolution, thus the reconstruction artifacts are similarly displayed. However, Applicant has appreciated that changes in density values (e.g., intensity variation) at artificially high resolutions, when displayed, may be perceived by radiologists and may be interpreted as, for example, tissue anomalies that may lead to misdiagnosis. By limiting the display resolution, density variation at resolutions higher than the actual resolution may be suppressed, preventing corresponding artifacts from the reconstruction process from being displayed to a viewer.

FIG. 3A illustrates a conventional technique for viewing display data. For example, projection data 305 may have been obtained by exposing an object to radiation from a plurality of view angles. The projection data 305 has an actual resolution related in part to the geometry of the detector array and radiation emission parameters (e.g., the in-plane resolution) and the number and position of view angles from which the object was obtained (e.g., the out-of-plane resolution). The projection data may have been obtained by performing exposures at a relatively small number of view angles (e.g., substantially fewer view angles than needed for full CT) to satisfy desired dose and/or time constraints. Accordingly, projection data 305 may have an asymmetric resolution (e.g., the in-plane and out-of-plane resolutions may be different).

A reconstruction 310 may be performed on projection data 305 to form reconstructed image data 315. The reconstruction may be performed according to a particular reconstruction resolution, illustrated schematically by the size of the volume elements (voxels) by which image data 315 is partitioned. The reconstruction algorithm may be configured to assign each voxel a density value (referred to as the intensity of the voxel), based on the information in the projection data. As shown, the reconstruction resolution in the XY plane is greater than the resolution in the z-direction (i.e., the partitioning in the XY plane is smaller than the partitioning in the z-direction). This may be partially due to the fact that projection data was obtained from a relatively small number of view angles (e.g., from between 1-30 view angles).

In FIG. 3A, reconstruction 310 may be configured to reconstruct image data at a resolution higher than the actual resolution of the projection data. For example, reconstruction at a higher resolution may be necessary to appropriately reconstruct the projection data at the resolution and geometry at which it was obtained. As a result, reconstruction 310 may assign different density values to adjacent voxels even though information about density changes at that resolution is not available in the projection data. That is, the projection data may not contain enough information to distinguish density at the resolution of the reconstruction. Accordingly, some variation in density in the reconstructed image data may be artifacts of reconstruction, rather than an accurate rendering of the imaged object.

Conventionally, image data is displayed at the same resolution as it was reconstructed. For example, display procedure 320 may display reconstructed image data 315 at the same resolution, as shown schematically by display image data 325. Conventional understanding is that image data should be displayed at the highest resolution possible to display the maximum amount of information. For example, the conventional belief is that the higher resolution display data provides richer information on which a radiologist can perform a diagnosis. However, it may be advantageous to display image data at a resolution commensurate with eliminating at least some reconstruction artifacts, typically less than the maximum available resolution in the reconstructed image data.

As illustrated, a three-by-three voxel neighborhood 317 is shown with exemplary density values shown as greyscale intensities (i.e., voxel intensities). However, the projection data may not have the resolution to distinguish different density values at this high a resolution, and at least some of the variation in density values shown is an artifact of the reconstruction process. When the image data is displayed at the same resolution, the variation in density values is perceptible (see neighborhood 317'), even though the variation is not physically supported in the projection data. A radiologist may view this variation and interpret the variation as some sort of structure or feature in the image (e.g., as a tissue anomaly). In a breast imaging procedure, for example, the lighter intensity at the center of neighborhood 317' may be interpreted as a micro-calcification, early stage tumor, etc., even though the variation that gave rise to the intensity may be artificial.

By limiting the display resolution, density variation at resolutions higher than the actual resolution may be suppressed, preventing corresponding artifacts from the reconstruction process from being display to a viewer. Limiting the displayed resolution to substantially the actual resolution may reduce the opportunity for a radiologist to misinterpret reconstruction artifacts as salient structure in the image. In some embodiments, the display resolution is limited so that variation is not displayed at resolutions higher than are supported by the projection data.

FIG. 3B illustrates concepts related to limiting the display resolution, in accordance with some embodiments of the present invention. In FIG. 3B, the projection data 305, and reconstruction image data 315 may be similar to that shown in FIG. 3A. Accordingly, the projection data may be reconstructed at a resolution higher than the actual resolution. However, rather than displaying the image data at the reconstruction resolution, the display procedure 320' displays the image data 325' at a reduced display resolution, at least with respect to the z-axis where the actual resolution is particularly limited and therefore more likely to result in image data artifacts after reconstruction. In some embodiments, the resolution reduction is performed so that the display image has no variation not accounted for in the projection data. As a result, any variation in the display image data will be a result of and supported by information in the projection data.

The display resolution may be reduced by, for example, considering density values in a neighborhood of voxels and computing a single density value from the neighborhood. The size of the neighborhood may be selected in view of the amount of resolution reduction required. In addition, the neighborhood selected to transform into a single voxel density value may be chosen in any direction, even if a reduction in resolution is not desired along the corresponding axis. As shown by the voxel sizes in FIG. 3B, the resolution in the z-direction is less for the display image data 315 than for the reconstruction image data 325. The resolution reduction in the z-direction may be achieved, for example, by averaging three adjacent voxel density values in the z-direction to produce a single voxel having the computed average as its density value to reduce the resolution in the z-direction by a factor of three.

Resolution reduction may be achieved by selecting any size and/or dimensioned neighborhood, and performing any type of computation on the neighborhood, as the aspects of the invention are not limited in this respect. As illustrated, the density variation in the z-direction in the reconstructed image data (e.g., artifacts from the reconstruction) are suppressed in the display image data, thus preventing the artificial variation from being misinterpreted by a viewer of the image data (e.g., a radiologist analyzing and/or otherwise diagnosing the image data).

Figure 4:
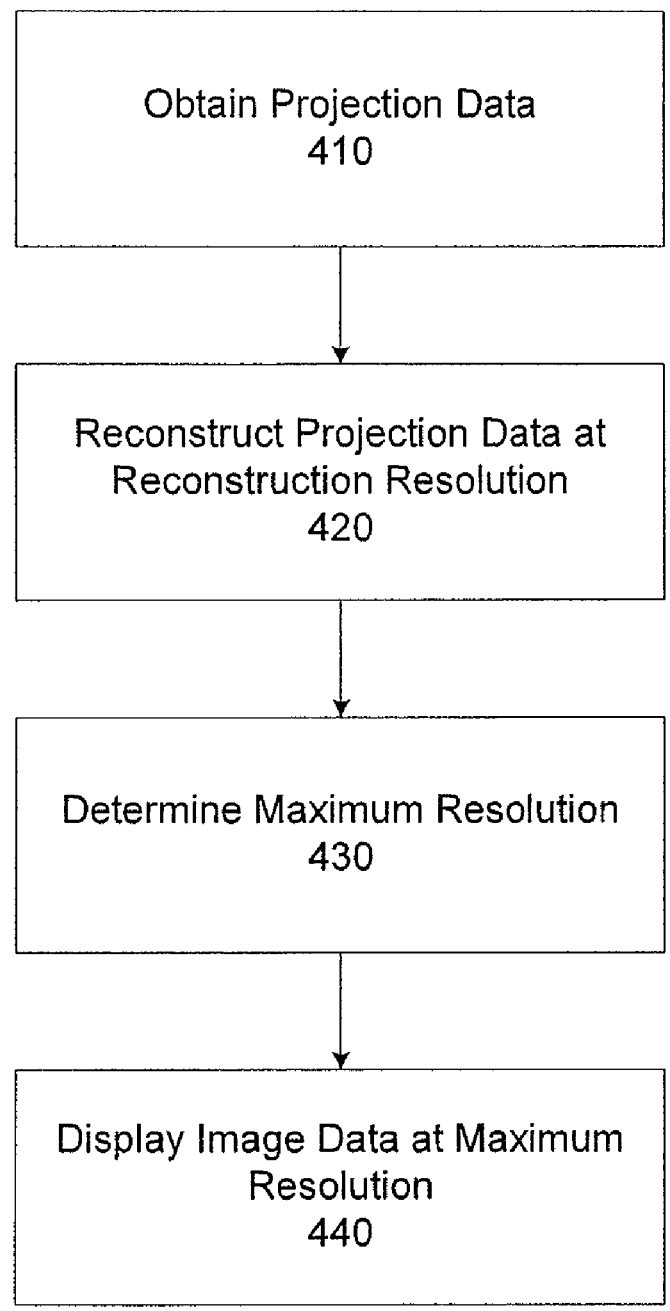
FIG. 4 illustrates a method of reducing the display resolution, in accordance with some embodiments of the present invention.

FIG. 4 illustrates a method of reducing the display resolution, in accordance with some embodiments of the present invention. In act 410, projection data is obtained by exposing an object to radiation at a plurality of view angles. In some embodiments, the projection data is obtained from a relatively limited number of view angles (e.g., between 1-30 view angles distributed uniformly or non-uniformly about the object) to satisfy desired safety and/or time constraints. Accordingly, in some embodiments, the projection data may have an asymmetric actual resolution (e.g., the in-plane resolution may be higher than the out-of-plane resolution). However, the projection data may be obtained in any manner, as the aspects of the invention are not limited in this respect.

In act 420, the projection data is reconstructed at a resolution higher than the actual resolution along at least one axis. For example, the projection data may be reconstructed at a resolution appropriate for reconstructing asymmetric resolution projection data obtained at a particular geometry. The reconstruction may be performed according to any desired reconstruction algorithm capable of assigning density values to voxels at the reconstruction resolution. In some embodiments, the reconstruction resolution is asymmetric due to, for example, acquiring the projection data at a relatively small number and range of view angles and the reconstruction resolution is higher than the actual resolution along the asymmetric axis only (e.g., the out-of-plane resolution).

In act 430, a maximum resolution is determined, along at least one axis, for the display resolution such that artificial variation in the density values is substantially suppressed. For example, the maximum resolution may correspond to the maximum resolution supported by the projection data. This maximum resolution may be determined by considering the geometry of the imaging equipment, the number and distribution of view angles from which the projection data was obtained, the parameters of the emitted radiation, etc. For image data having asymmetric resolution, the maximum resolution may be different along each axis of the reconstructed image data. There may be one or more axes over which the maximum resolution is the same or substantially the same as reconstruction resolution. For example, the maximum in-plane resolution may be the same as the in-plane reconstruction resolution, while the maximum out-of-plane resolution may be less than the out-of-plane reconstruction resolution.

In act 440, the image data is displayed at or below the maximum resolution along each axis of the image data. The resolution reduction may be achieved by any method, some exemplary methods of which are described in further detail below, without limitation. By displaying the image data at or below the determined maximum resolution, some of the density variation resulting from high resolution reconstruction may be suppressed, preventing that particular variation from being displayed and potentially misinterpreted by a viewer of the image.

As discussed above, there may be a variety of reasons to reduce the display resolution of image data. For example, the display resolution may be reduced to facilitate the prevention of false high resolution variations from being displayed to a viewer, as discussed in the foregoing. In addition, it may be desirable to reduce the display resolution to display the image data on lower resolution screens, monitors or other displays. Moreover, it may be desirable to reduce the display resolution so that multiple images may be simultaneously displayed. However, conventional methods of reducing the display resolution may obscure salient or otherwise important information. For example, conventional averaging techniques (such as the above-mentioned voxel averaging technique) tend to remove high frequency information that may be important to accurate medical diagnosis, or other image analysis.

Figure 5A:
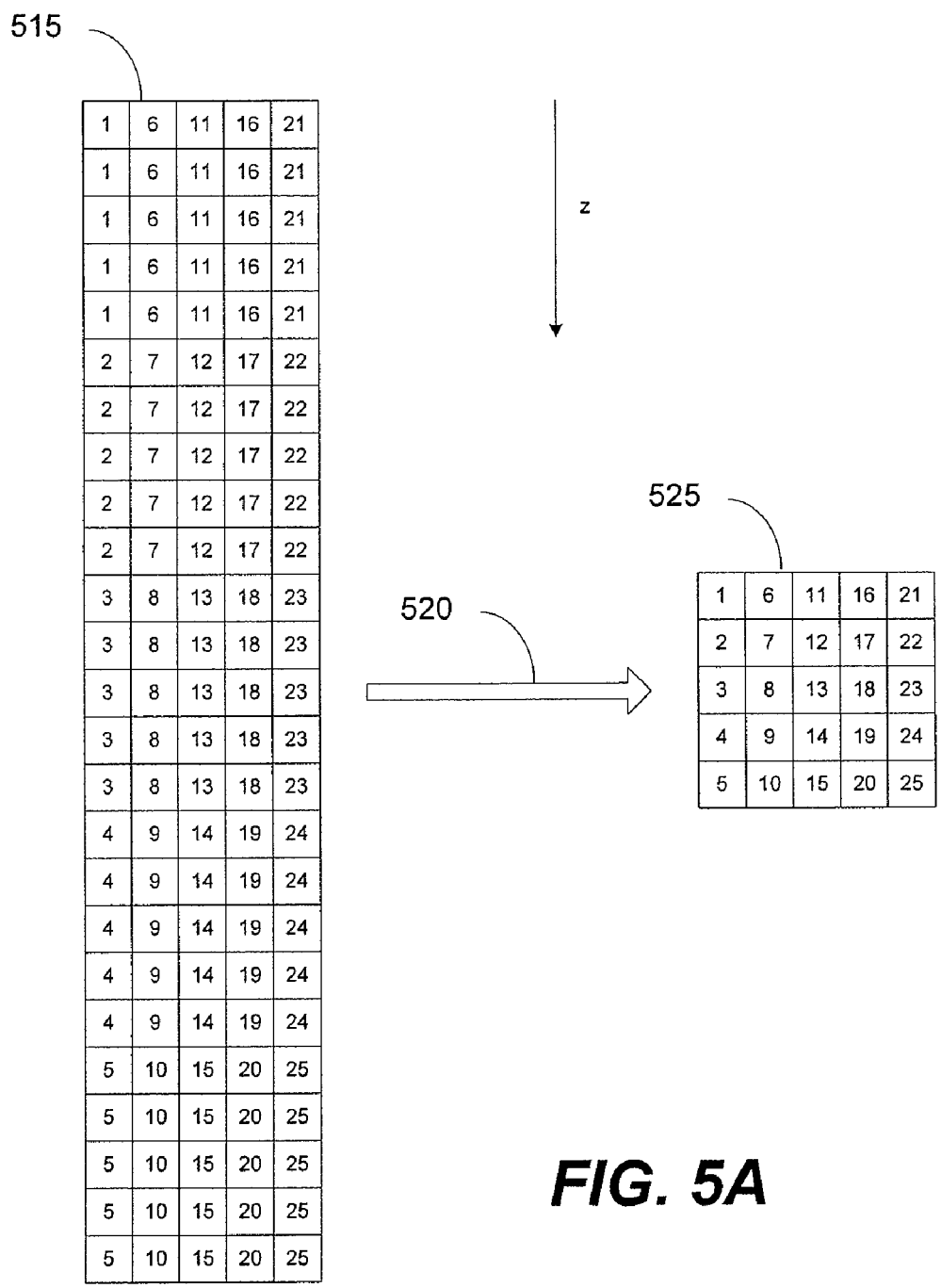
FIGS. 5A, 5B and 5C are diagrams illustrating transforming voxel neighborhoods in one, two and three dimensions, respectively.

FIG. 5A illustrates a method of reducing the display resolution of image data in one dimension. Image data 515 represents a portion of an image of an object obtained from exposing the object to radiation from a plurality of view angles. The image data comprises a plurality of pixels (generally in 2D) or voxels (generally in 3D) represented as cells in an array, each having a value (referred to as intensity) indicative of the density of the object at a location associated with the respective voxel. The term "intensity" refers herein to any vector or scalar value that indicates relative degree. To reduce the resolution, a collection of (usually contingious) voxels, referred to as a neighborhood may be transformed into a single voxel having an intensity representative of the neighborhood. Thus, each neighborhood of voxels may be reduced to a single voxel, thus reducing the resolution.

In FIG. 5A, the display resolution is reduced by a factor of five in the z-direction, from image data 515 to reduced resolution display image data 525. Accordingly, the image data may be grouped into neighborhoods of contiguous voxels in the z-direction. Twenty-five such neighborhoods are shown in FIG. 5A, each voxel being labeled with the number of the neighborhood with which it is associated. As discussed above, resolution reduction may be achieved by transforming a neighborhood of voxels to a single voxel, and more particularly, transforming the density values of a neighborhood to a single representative density value, illustrated by transformation 520 in FIG. 5. Thus in the reduced resolution image data 525, each neighborhood 1-25 is represented by a single voxel labeled with the respective neighborhood, and having an intensity representative of the neighborhood, as discussed in further detail below.

Figure 5B:
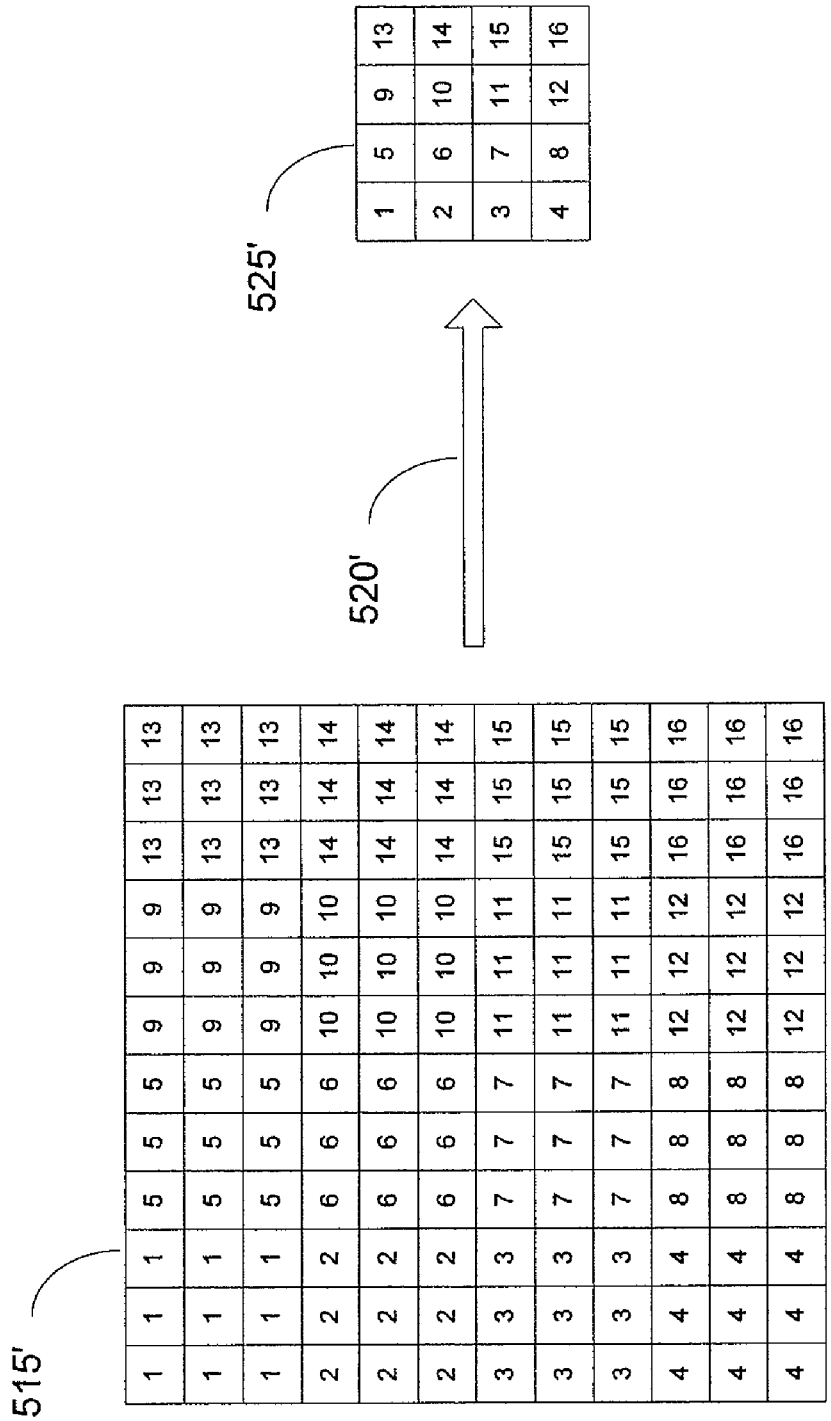
Figure 5C:
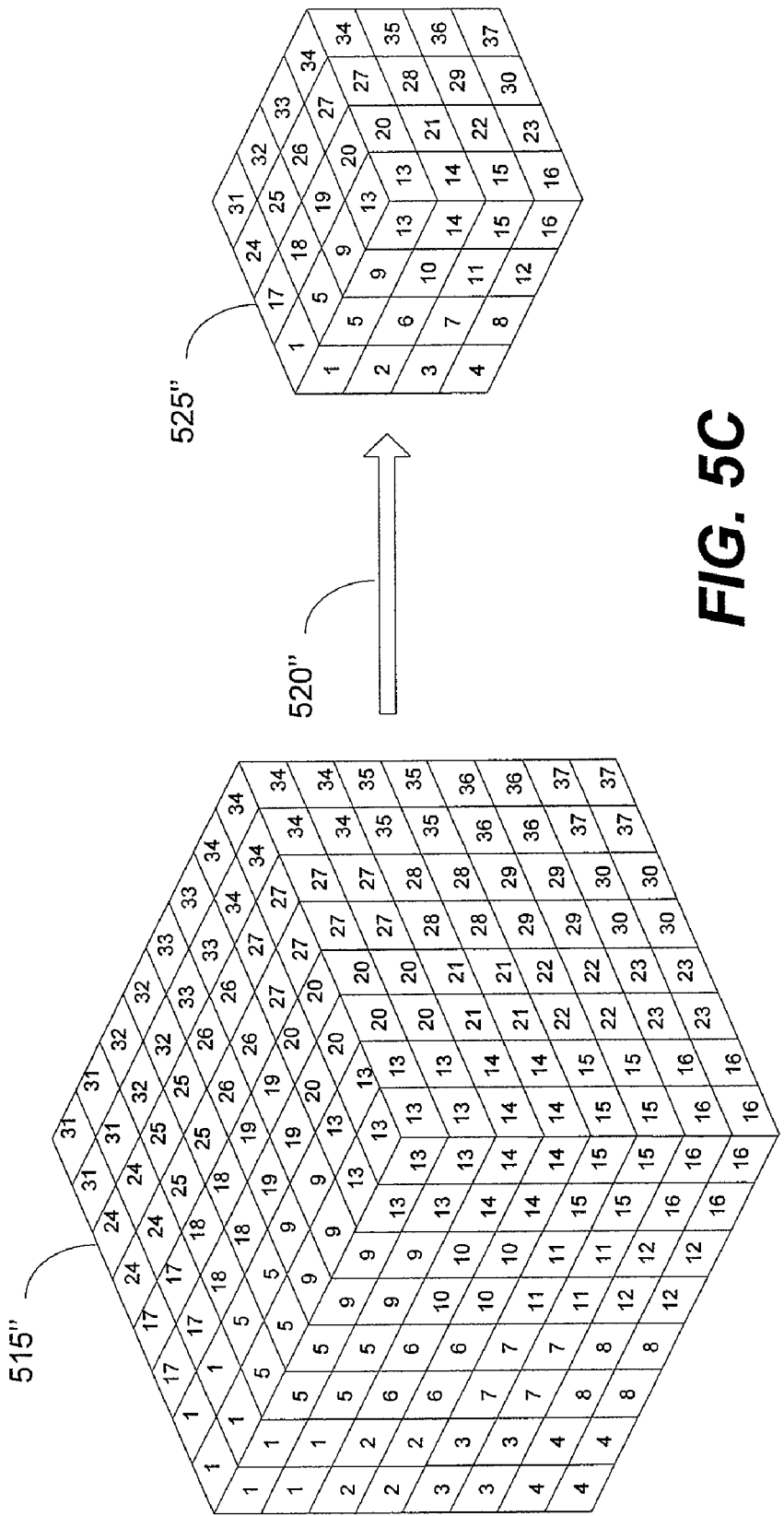

It should be appreciated that resolution reduction may be performed in any number of dimensions. For example, FIG. 5B illustrates a resolution reduction by a factor of three in two dimensions. In particular, image data 515' is divided into a plurality of two-dimensional neighborhoods labeled 1-16. Image data 515' is transformed into image data 525' at the reduced display resolution by transforming the neighborhood density values to a respective representative density value according to transformation 520'. FIG. 5C illustrates a resolution reduction by a factor of two in three dimensions. In particular, image data 515" is divided into a plurality of three-dimensional neighborhoods. Image data 515" is transformed into image data 525" at the reduced display resolution by transforming the neighborhood density values to a respective representative density value according to transformation 520'.

It should be appreciated that resolution reduction need not be the same in every direction when performed in multiple dimensions, as the aspects of the invention are not limited in this respect. For example, with image data having an asymmetric resolution, the resolution reduction in each direction may be different (e.g., the in-plane resolution may be reduced by a smaller factor than the out-of-plane resolution with respect to the reconstruction resolution). In addition, neighborhoods may be chosen to be of any size or shape and are not limited to including contiguous voxels in the one or more directions in which the resolution is to be reduced.

Figure 6:
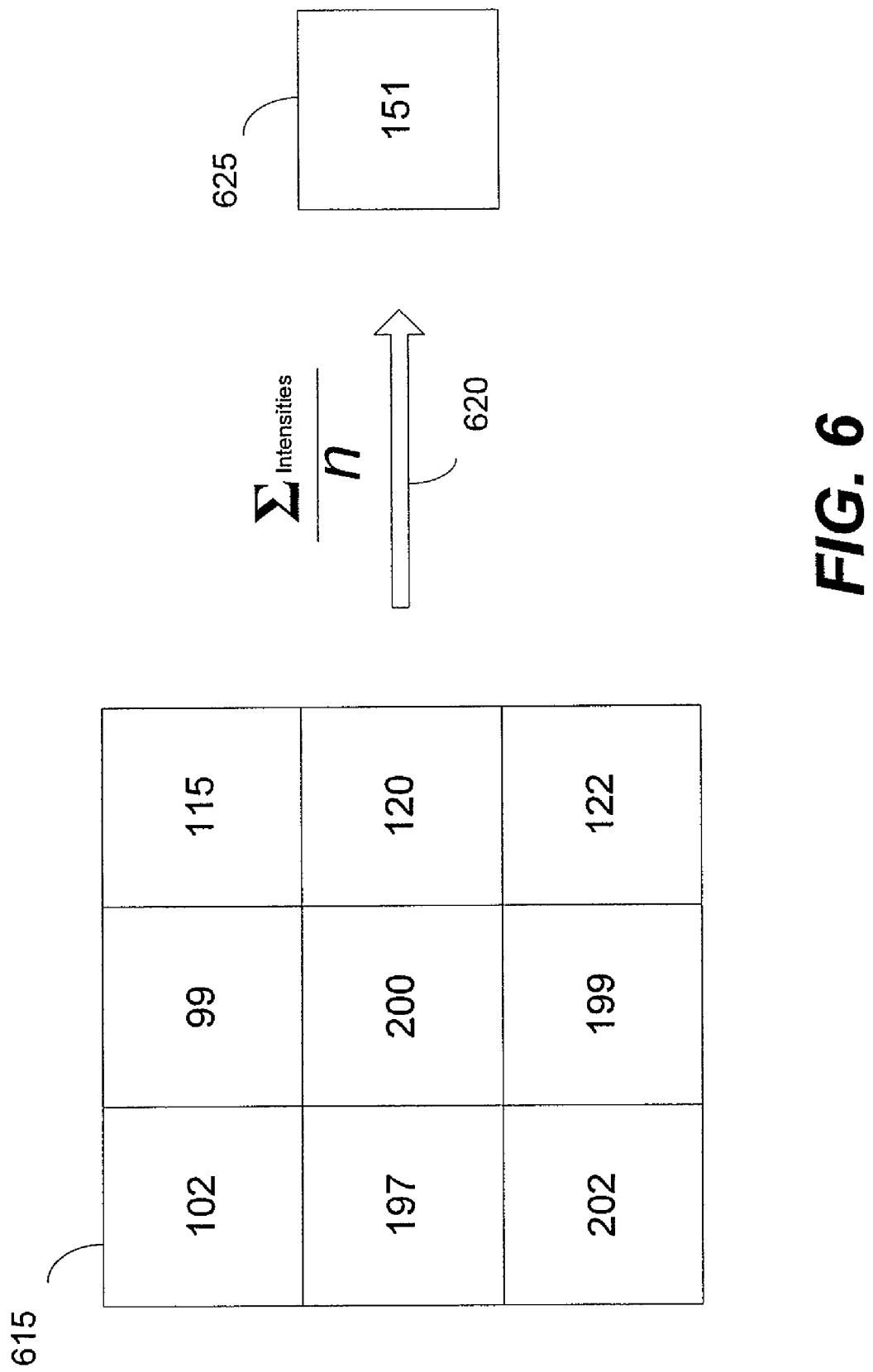
FIG. 6 is a diagram illustrating transforming a voxel neighborhood using an averaging transformation.

In conventional resolution reduction, the transformation from reconstruction image data to display image data is often an averaging operation on the neighborhood intensities, as shown by the exemplary transformation 620 illustrated in FIG. 6. In particular, FIG. 6 illustrates a neighborhood 615 which may be a portion of reconstruction image data. Each voxel is labeled with its associated density value. Transformation 620 takes the average of the neighborhood intensities to form a representative voxel 625 having the average as its density value (i.e., the representative intensity for the neighborhood is the average of the neighborhood intensities).

However, simple averaging may obscure salient information or features in the object (e.g., has the effect of applying a low-pass filter to the neighborhood). For example, in the neighborhood 615, there is a cluster of relatively high density material in the bottom left hand corner that may be related to important information. The averaging, however, suppresses significant information regarding this high density cluster by considering uniformly the contributions from each voxel in the neighborhood, removing some of the high frequency information during the display procedure.

Figure 7:
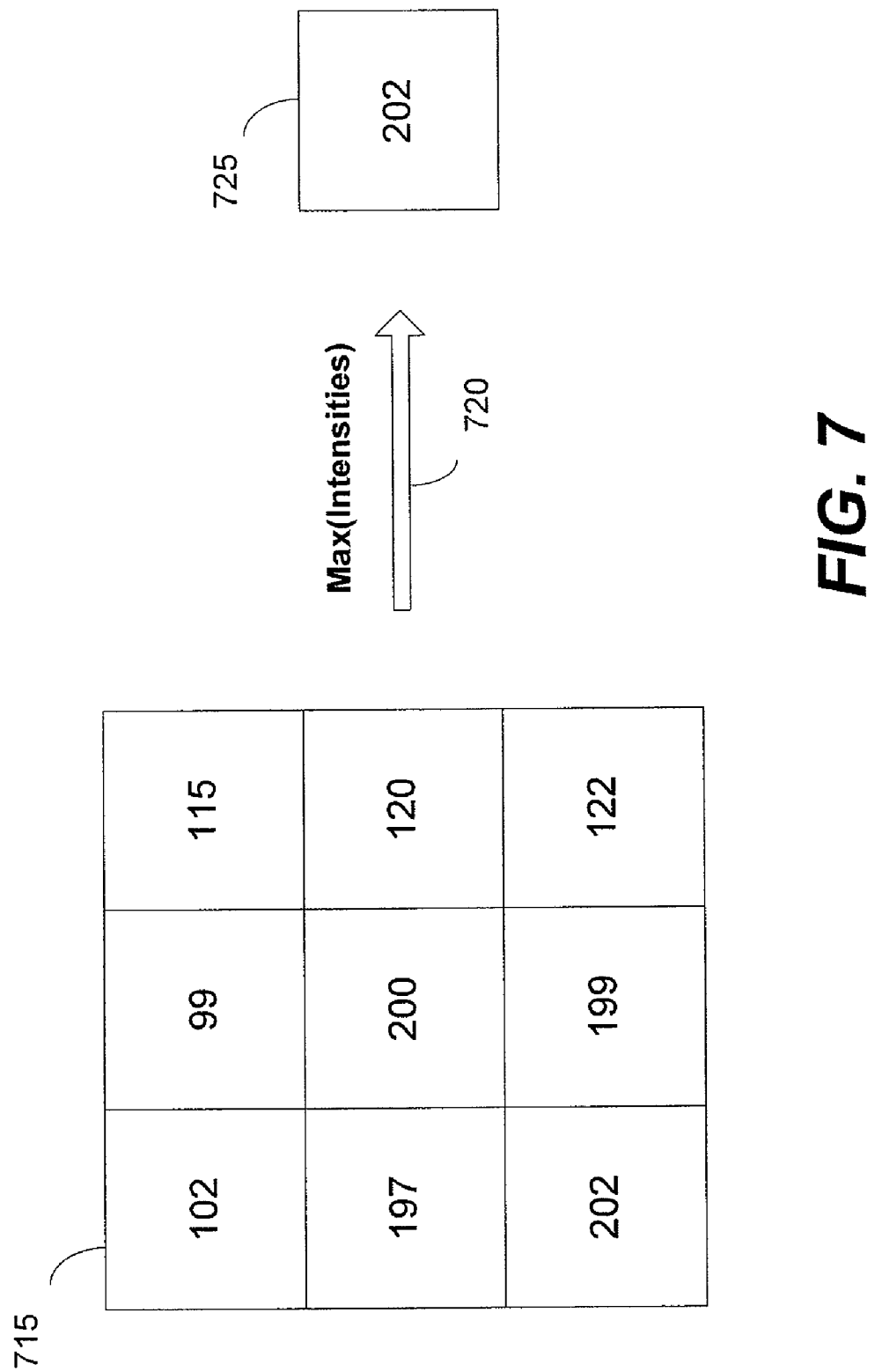
FIG. 7 is a diagram illustrating transforming a voxel neighborhood using a maximum intensity value transformation, in accordance with some embodiments of the present invention.

Numerous transformations that may be more suitable for resolution reduction. In some embodiments, for example, the maximum intensity value (MIV) in a neighborhood may be selected as the representative intensity, as shown by the exemplary transformation illustrated in FIG. 7. In particular, neighborhood 715 may be image data from a portion of an image to be displayed. Transformation 725 takes the maximum intensity value of the neighborhood (202) and assigns the MIV as the representative intensity to voxel 725. In some embodiments, a function is applied to the neighborhood to transform the intensities, followed by one or more operations to convert the neighborhood intensity values to a single intensity value. The inverse of the function applied to transform the neighborhood may then be performed on the single value to transform the single value into the representative intensity assigned to the single voxel representing the neighborhood.

Figure 8:
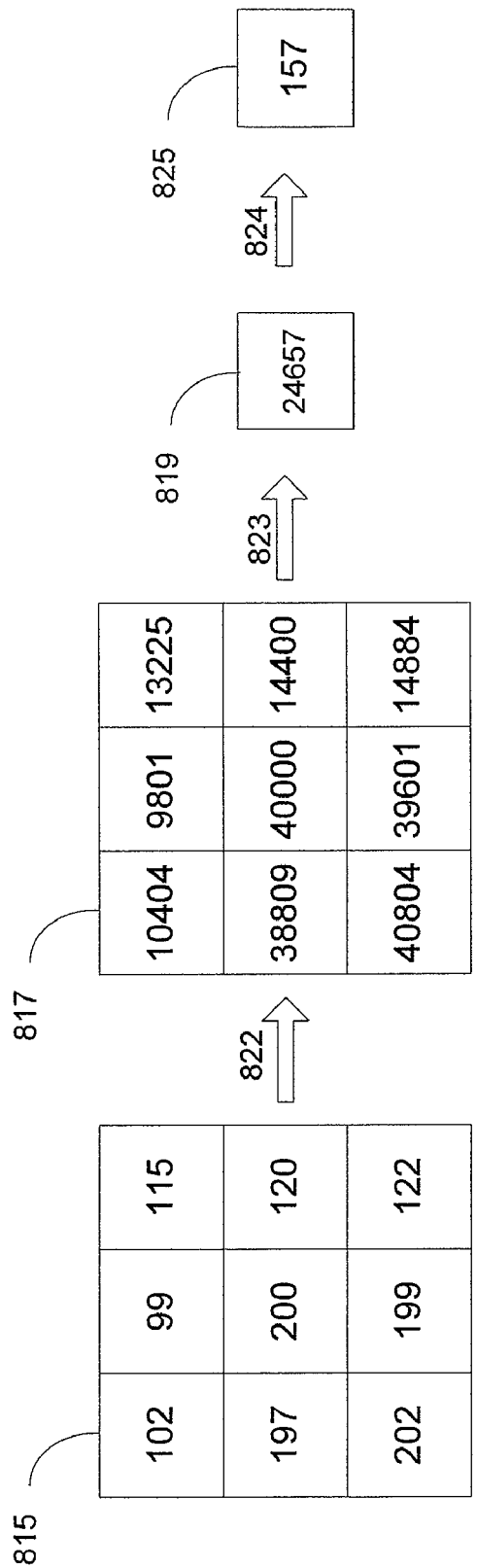
FIG. 8 is a diagram illustrating transforming a voxel neighborhood using a root mean square transformation, in accordance with some embodiments of the present invention.

FIG. 8 illustrates a using a power function, an average operation and an inverse power function (root function) to determine a representative intensity value for a neighborhood (e.g., to perform a root mean square transformation). In particular, function 822 transforms neighborhood 815 to neighborhood 817 by taking the square of the intensity values in the neighborhood. Operation 823 transforms neighborhood 817 into a single intensity value 819 by taking the average of the squared intensities, and inverse function 824 transforms the single intensity value 819 into the representative intensity value 825 by taking the square root of the average. Accordingly, the intensity value 157 is root mean square of the neighborhood of intensities (rounded to the nearest integer). The root mean square weights higher density values with more significance (i.e., via the power function), which may be associated with subject matter of interest in an image. In some instances, the root mean square transformation avoids the blurring effect of pure averaging by emphasizing the contribution of higher intensity values.

Figure 9:
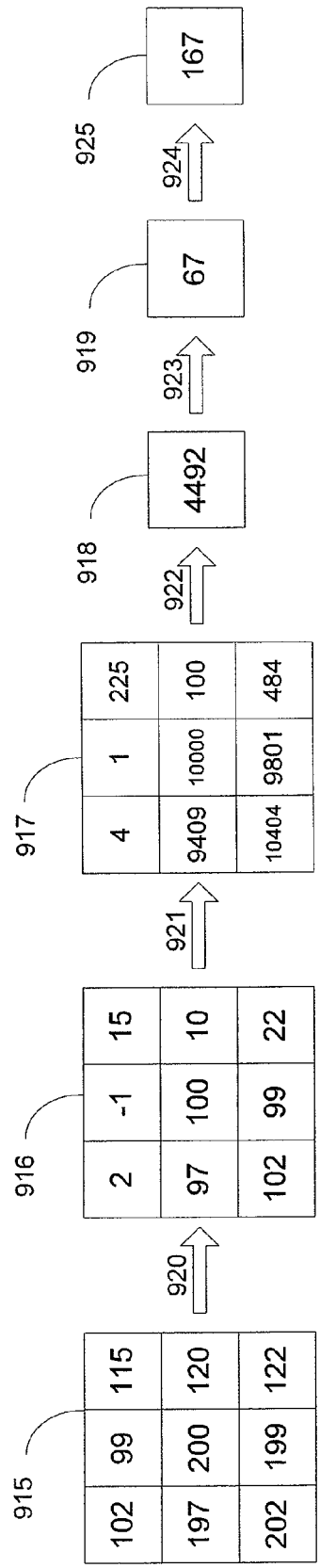
FIG. 9 is a diagram illustrating transforming a voxel neighborhood using a shifted root mean square transformation, in accordance with some embodiments of the present invention.

FIG. 9 illustrates another method of transforming a neighborhood into a single intensity value to reduce the resolution, in accordance with some embodiments of the present invention. The method shown in FIG. 9 is similar to the method illustrated in FIG. 8 in that a root mean square operation is performed. However, prior to squaring the intensity values, function 920 shifts the intensity values by subtracting an offset from the neighborhood. After the offset has been subtracted from each intensity value in the neighborhood, the intensity values may be squared (transformation 921), and the average taken of the shifted and squared intensity values (transformation 922). The square root of the average may be performed (transformation 923), and the offset added back to the intensity value to form the representative intensity value for the neighborhood (transformation 924).

In some embodiments, the offset is related to a characteristic density of the object being imaged. By subtracting the offset from the neighborhood intensities before squaring, differences from the characteristic density are accorded even further significance in the transformation. In breast imaging, the density of the fatty tissue that comprises most of the breast material may be subtracted off from the neighborhood before performing the root mean square. In breast imaging, for example, it may be important to determine density anomalies with reference to the predominant surrounding tissue. By subtracting off density values characteristic of healthy breast tissue, the remaining values relative to the fatty tissue may be further emphasized. As a result, the removal of important information that often results from pure averaging may be mitigated in this respect. Other functions may be performed on the neighborhood before averaging to facilitate selecting a representative intensity value without obscuring important information in the image, as the aspects of the invention are not limited in this respect.

As discussed above, confusion resulting from the superposition of structure at different depths may be reduced by providing 3D images. In particular, the various methods described in the '828 and '848 patents may be used to provide 3D image data that can be viewed at different depths without structure from other depths obscuring the display. An operator may navigate through a 3D image, for example, by allowing an operator to control the depth at which the image is displayed. In conventional navigation controls, structure at different depths may appear and disappear abruptly as the operator progresses from one depth to another, resulting in a very unintuitive experience for the operator that may lead to incorrect diagnosis. Methods of displaying information such that depth transitions may appear more natural and intuitive may be beneficial.

Figure 10:
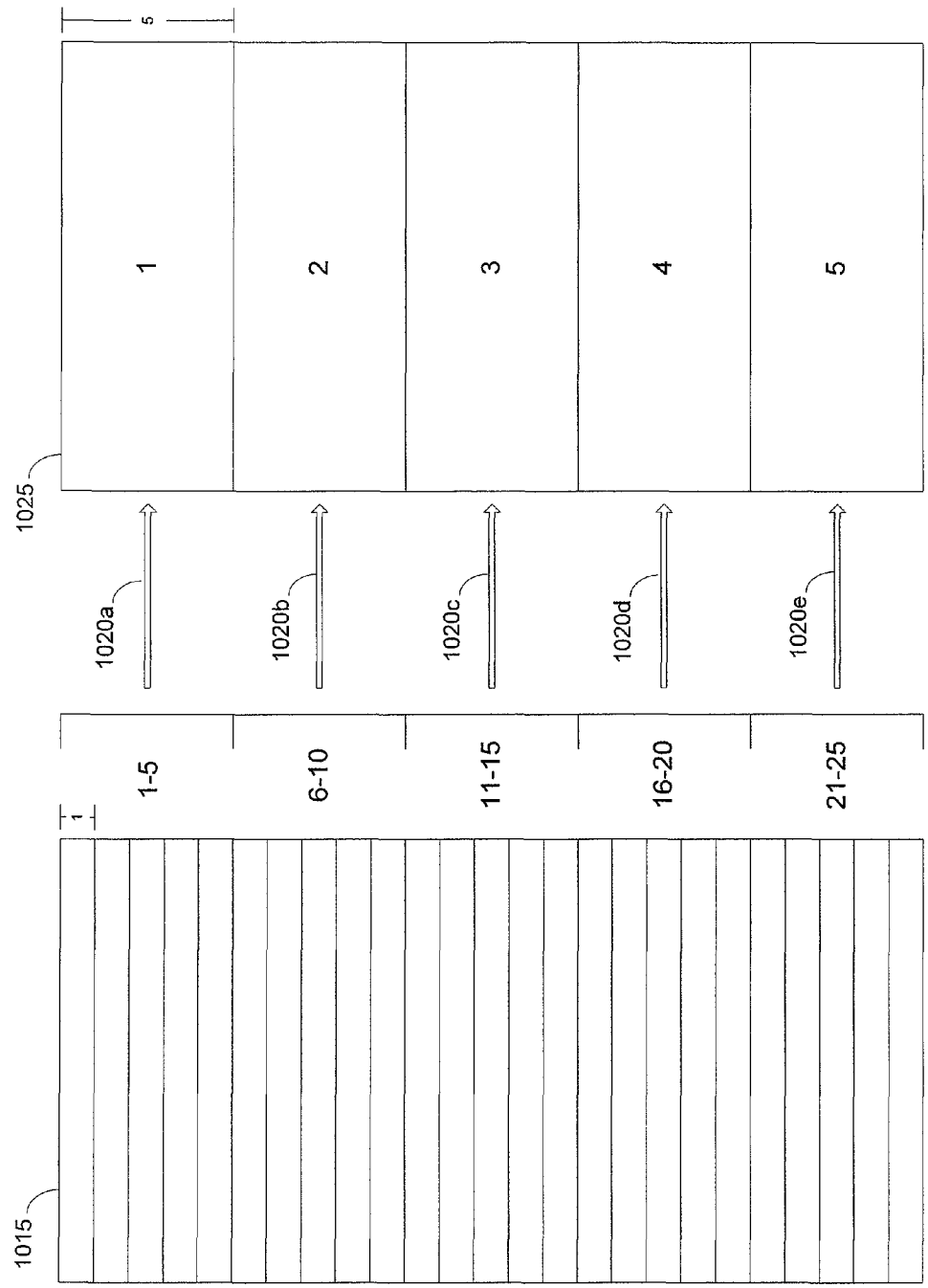
FIG. 10 is a diagram illustrating transforming slices of image data for display.

FIG. 10 illustrates one method of transforming reconstruction data to be displayed as an operator navigates through the image data. As discussed above, it may be beneficial to display data at a lower resolution than the resolution at which it was reconstructed. For example, reconstruction image data 1015 may be reconstructed at a reconstruction resolution having a single unit for each pixel in the z-direction (e.g., 1 mm slices). Each rectangle in the reconstruction data represents a slice of image data in the XY plane. The resolution in the XY plane is not illustrated.

Figure 16:
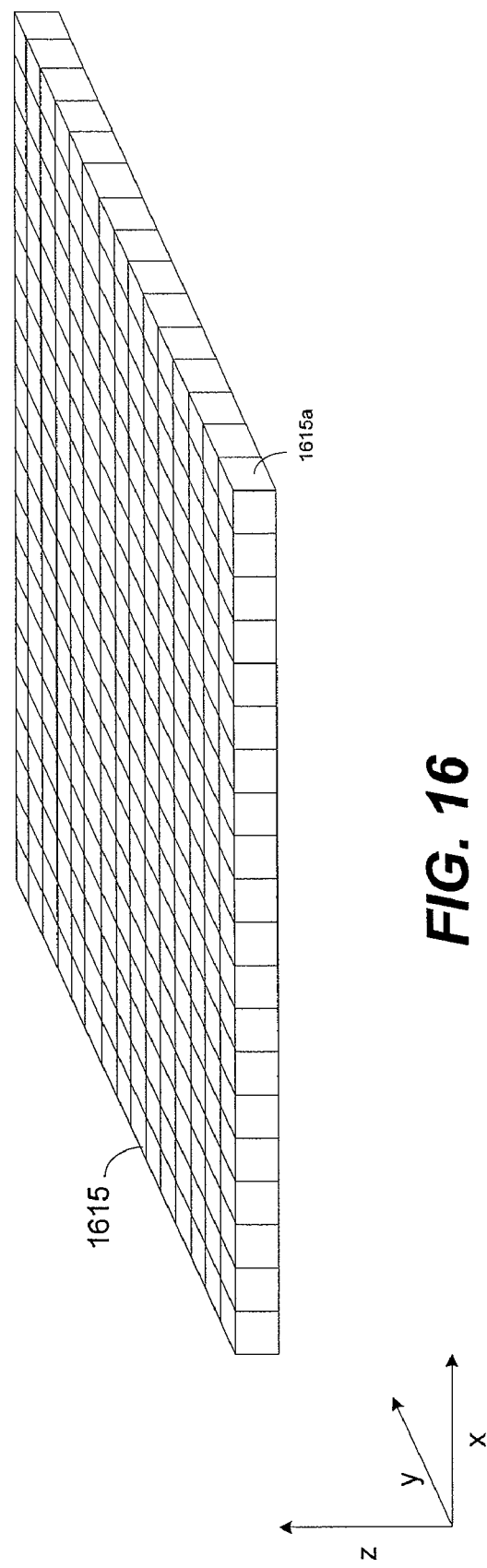
FIG. 16 is a schematic illustration of a slice of image data.

The term "slice" refers to a planar section of image data having dimensions in voxel units, with a single voxel in one of the dimensions (e.g., a slice may have dimensions N×M×1 voxels for a 3D slice). For example, FIG. 16 illustrates an exemplary slice 1615 comprising a plurality of voxels 1615a, the slice having dimensions 20×15×1 voxels in the x-direction, the y-direction and the z-direction, respectively. It should be appreciated that N and M may be any number and may be of the same or different value. In general, each voxel in a slice has an associated intensity, for example, indicative of a density value for a location in space represented by the corresponding voxel.

Display image data 1025 is being displayed at a display resolution that has been reduced by a factor of five. As with the reconstruction image data, each rectangle in the schematic representation of display image data 1025 represents a slice of display image data in the XY plane. Each slice of display data may be generated by transforming (e.g., transformations 1020a-920e) intensity values in the corresponding five slices (e.g., a five slice neighborhood) to obtain representative pixel values. For example, to display image data in the first slice of display image data 1025, the intensities values in slices 1-5 of reconstruction image data 1015 may be transformed by transformation 1020a to arrive at pixel intensities representative of pixel intensities in a five-slice neighborhood. Similarly, the intensities in the second slice of display image data 1025 may be transformed from slices 6-10 of the reconstruction image data, and so on down through the image. The transformation may be an average, a maximum intensity value, a root mean square, or any other transformation (e.g., any one or more combination of transformations described above) that transforms neighborhood density values to representative density values.

When an operator navigating through the image data navigates, for example, from slice 1 to slice 2 of display image data 1025, the pixel intensities change because pixel intensities in slice 1 of display image data 1025 are computed using reconstruction slices 1-5 of reconstruction image data 1015, and the pixel intensities of slice 2 of display image data 1025 are computed using reconstruction slices 6-10 of reconstruction image data 1015. As a result, as the intensities change, structure may appear and disappear abruptly as the operator navigates up and down through the display image data, providing an unnatural and unintuitive display of the image data. For example, structure just beyond the current viewing depth may be invisible until abruptly appearing as the operator scrolls to the next discrete slice of the display data. The abrupt changes may make it difficult to synthesize how the structure at the different depths are associated and/or may make diagnostic analysis of the images confusing.

Figure 11:
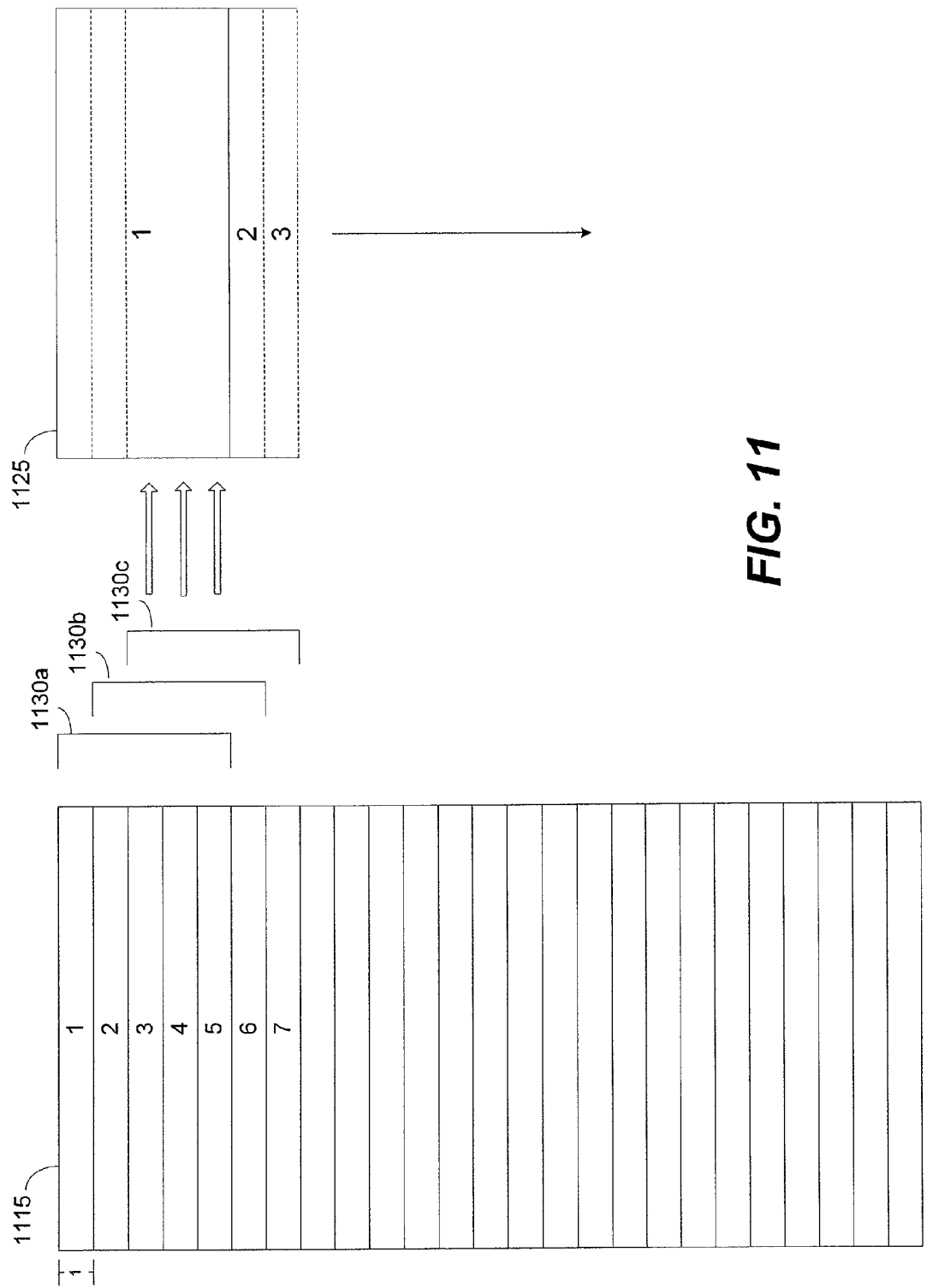
FIG. 11 is a diagram illustrating transforming slices of image data for display, in accordance with some embodiments of the present invention.

Applicant has appreciated that by blending in pixel intensity from reconstruction slices as an operator navigates through an image, the display viewed by the operator may be more intuitive and facilitate easier and more accurate diagnosis. FIG. 11 illustrates a method of displaying image data as an operator navigates around the image, in accordance with some embodiments of the present invention. As in FIG. 10, reconstruction image data may be reconstructed at a reconstruction resolution having 1 unit slices in the z-direction, and displayed at a display resolution reduced by a factor of five (e.g., 5 unit resolution). However, as an operator navigates in the z-direction, pixel intensities get transformed according to a sliding window that blends in slices at the reconstruction resolution, rather than at the display resolution.

For example, the pixel intensities of slice 1 of display image data 1125 may be computed from slices 1-5 of the reconstruction image data (i.e., transformed from pixel intensities in slices within window 1130a). However, as the image data is viewed at increasing depths, the pixel intensities of the reconstruction data get rolled in as the data is displayed at increasing depths. Thus, as an operator navigates deeper by one unit of reconstruction resolution, pixel intensities in slices within window 1130b (which slides in conjunction with the operator's navigation depth) are transformed to generate representative pixels in the corresponding slice of the display image data (e.g., the pixel intensities are transformed from slices 2-6 of the reconstruction image data). Accordingly, the window from which pixel intensities are transformed follows the navigation up and down through the data at the reconstruction resolution, to effect more gradual changes in intensity. The smoother transition may assist in better synthesizing information from different slices, and may facilitate a more intuitive viewing experience that aids in more accurate diagnosis. It should be appreciated that pixel intensities from slices within the window may be transformed according to any transformation, as the aspects of the invention are not limited in this respect.

Figure 12:
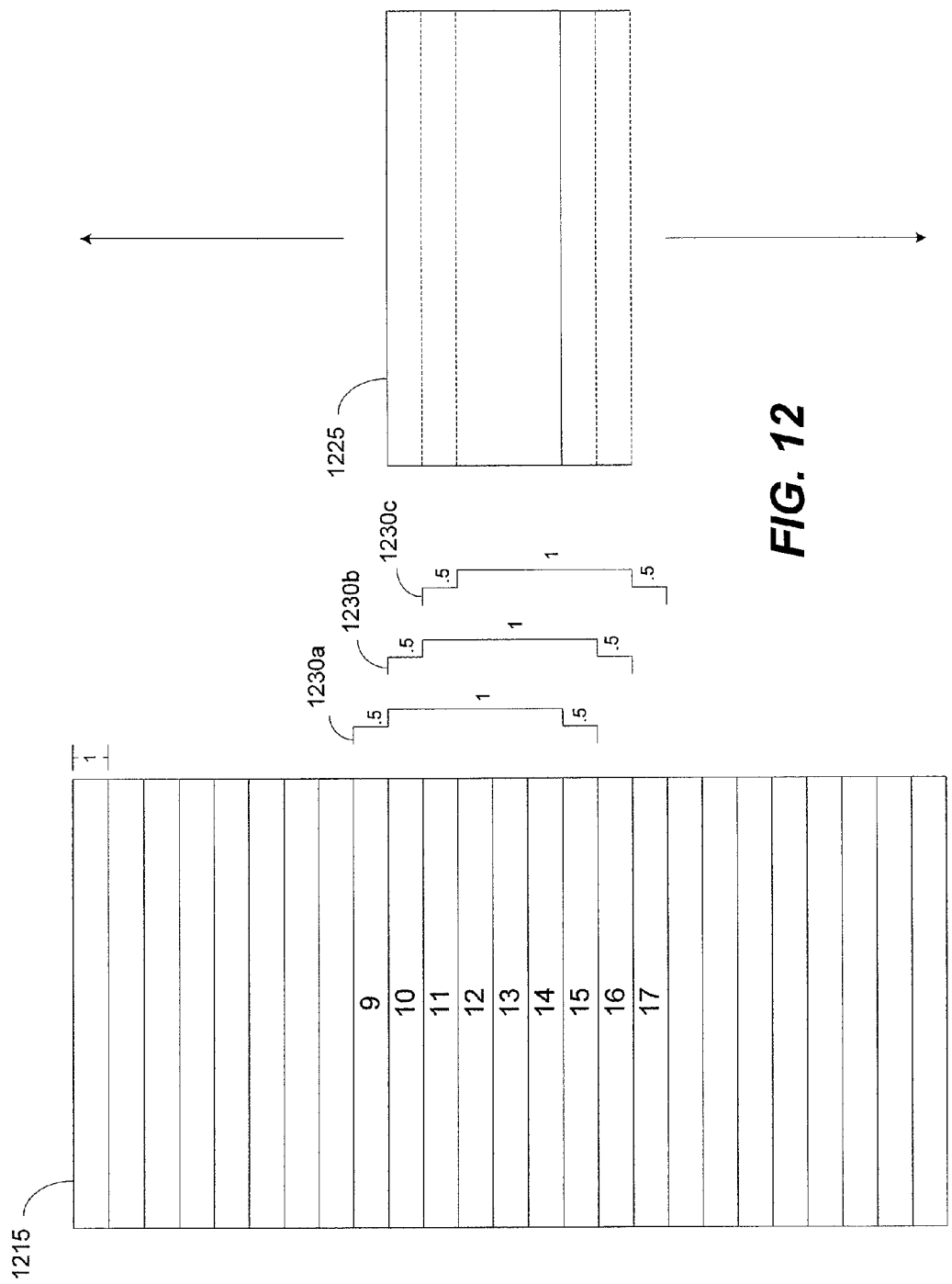
FIG. 12 is a diagram illustrating transforming slices of image data for display, in accordance with some embodiments of the present invention.

In FIG. 12, illustrates another method of transforming reconstruction data to display data during image navigation, in accordance with some embodiments of the present invention. The method in FIG. 12 may be similar with respect to FIG. 11 in that a sliding window is used to transform reconstruction image data to display image data at a reduced resolution. In particular, as an operator navigates to a new depth at a scale of the reconstruction resolution, pixel intensities from slices within the sliding window are transformed to representative pixel intensities at the reduced resolution.

However, window 1230 in FIG. 12 may consider a larger number of slices. In particular, in FIG. 11, window 1130 transformed pixel intensities from a number of slices equal to the resolution reduction factor (e.g., window 1130 transformed pixel intensities from 5 single unit slices to achieve a resolution reduction by a factor of five). In FIG. 12, a resolution reduction by a factor of five may still be achieved, however, window 1230 considers pixel intensities from more than the corresponding five slices (i.e., from more than the corresponding neighborhood). In particular, window 1230 considers an additional slice on both sides of the corresponding neighborhood. However, to avoid having the pixel intensities outside of the neighborhood contribute too significantly, the pixel intensities from slices inside and outside of the neighborhood may be weighted differently.

In FIG. 12, pixel intensities from slices inside the neighborhood fully contribute (i.e., have a weighting of 1), while pixel intensities from slices outside the neighborhood are weighted by 0.5. Applicant has appreciated that by considering pixel intensities outside of the neighborhood at a reduced weighting, structure just outside the neighborhood may be partially visible, enhancing the smoothness of structure transitioning in and out of view as an operator navigates through the image data. For example, an operator positioned at the illustrated depths in FIG. 12 will perceive (though perhaps faintly) intensity resulting from structure outside the five slice neighborhood (e.g., from slice 9 and 15). As the operator continues to navigate downward, the intensity contribution from slice 9 disappears, and the intensities from slice 15 transitions into the neighborhood and is fully weighted. In addition, pixel intensities from slice 10 and 16 are now on the periphery and contribute at half-weight. As a result, structure at different depths in the object may transition into and out of view more smoothly, making navigation of the image data more natural and intuitive.

Figure 13:
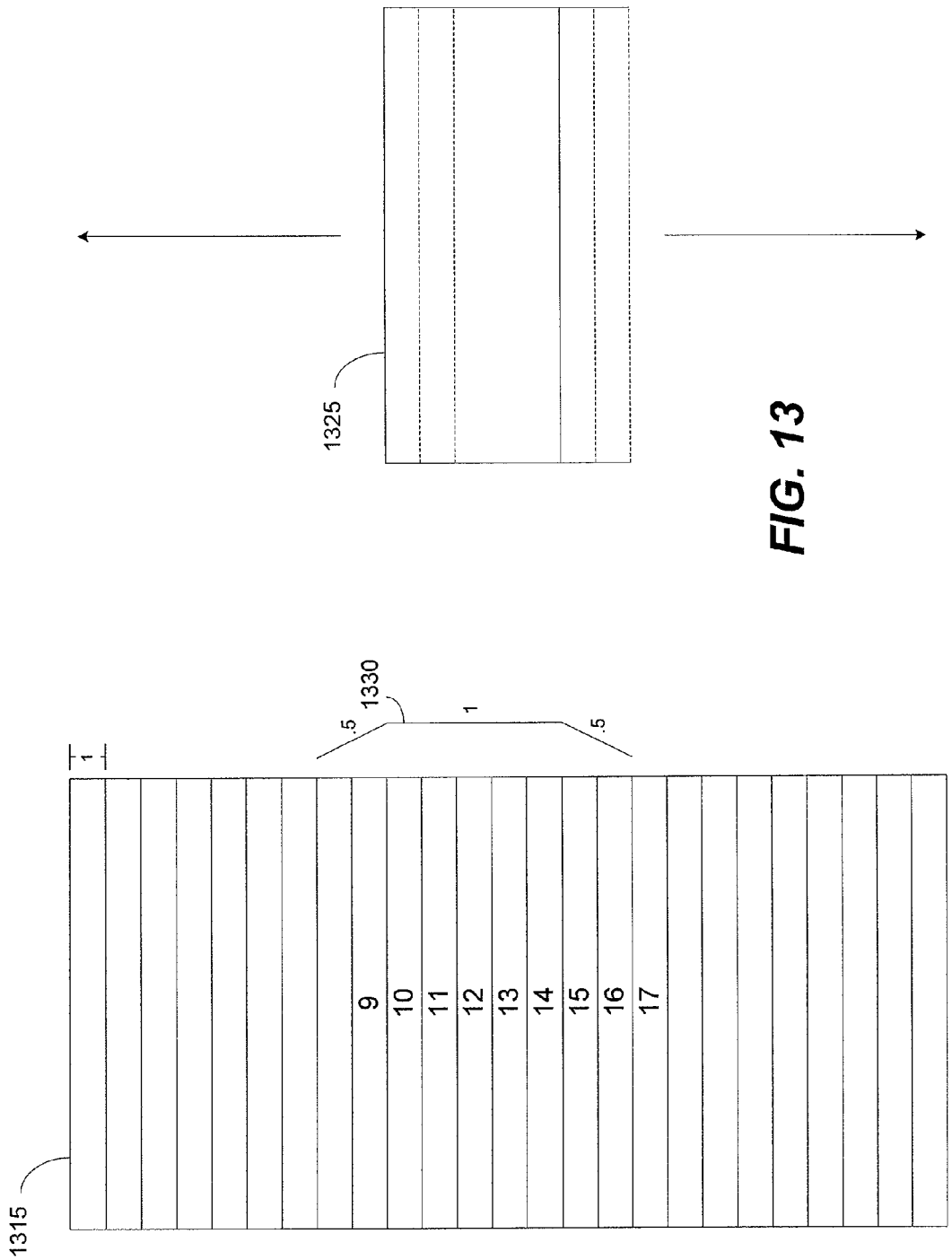
FIG. 13 is a diagram illustrating transforming slices of image data for display, in accordance with some embodiments of the present invention.

It should be appreciated that the weighting scheme used in FIG. 12 is merely exemplary, and any weighting scheme may be used (e.g., pixel intensities outside the neighborhood may be weighted by any desired amount). In addition, more than one peripheral slice on each side of the neighborhood may be considered, as the aspects of the invention are not limited in this respect. In particular, the window may be of any shape and size to incorporate a desired number of slices and any desired weights. For example, FIG. 13 illustrates a window 1330 that includes two peripheral slices on both sides of the neighborhood, treating each peripheral slice with a decreased weighting. In some embodiments, pixel intensities within the neighborhood are also weighted. For example, a window may be shaped like a triangle window or a Hanning window that weights pixel intensities of slices towards the center of the window with more significance than pixel intensities of slices more towards the periphery.

Figure 14:
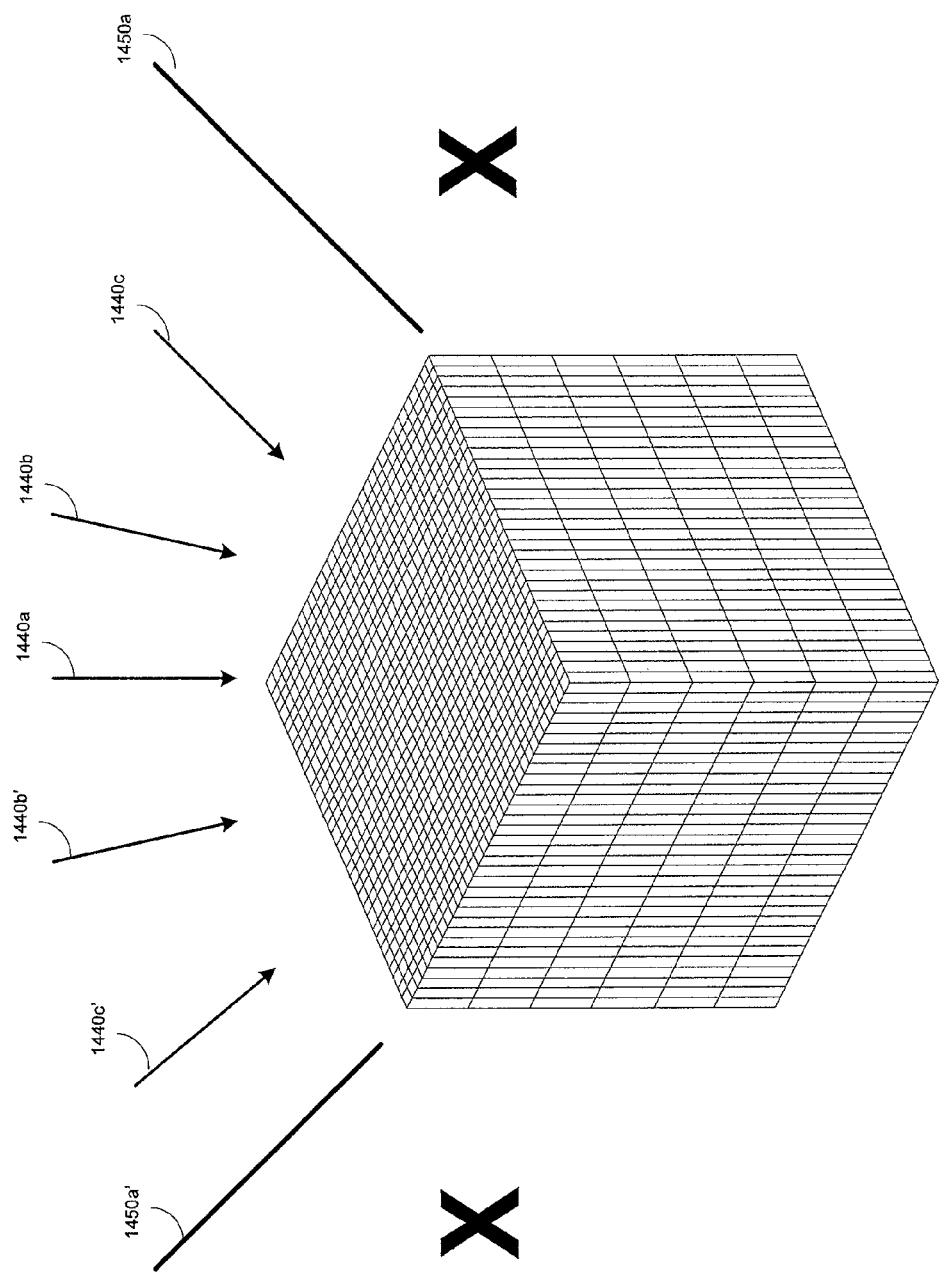
FIG. 14 is a diagram illustrating viewing image data from a plurality of angles, and preventing the image data from being viewed outside a range of angles, in accordance with some embodiments of the present invention.

Conventional software that allows a user to navigate through 3D image data typically allows motion in a single direction. For example, conventional software may limit an operator to viewing image data in the XY plane at successive slices. However, conventional software may not allow an operator to view the 3D data at different angles. FIG. 14 illustrates schematically 3D image data 1415. Conventional display software may allow an operator to view the image data in the XY plane from a direction substantially perpendicular to the plane. For example, an operator may view the XY plane from direction 1440$a$, and be permitted to view slices at successive depths in this direction only. However, some software may allow the user to view the image data from multiple views (e.g., to view the data from directions 1440$b$, 1440$b'$, 1440$c$, 1440$c'$, etc.), and permit navigation through the image data along those views.

Figure 15:
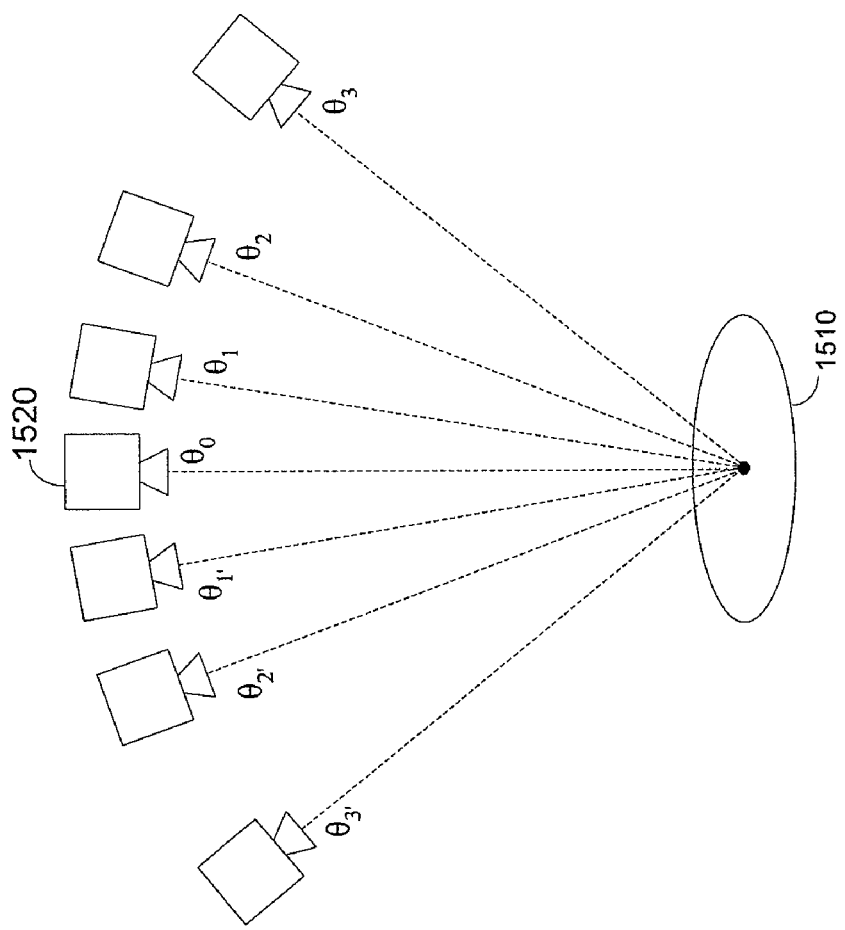
FIG. 15 is a diagram illustrating obtaining projection data from a limited number of projections across a range to determine a boundary outside of which image data should not be viewed, in accordance with some embodiments of the present invention.

However, in some instances, an operator should be prevented from viewing data at angles in which projection data was not obtained. For example, FIG. 15 illustrates an exemplary set of view angles from which projection data was obtained. Because projection data was not obtained at angles beyond angles $\theta_3$ and $\theta_{3'}$, and operator should not be allowed to view the data at angles beyond the boundaries at which the projection data was obtained to avoid displaying data that has no support in the projection data (e.g., to avoid displaying data that is artificial). Referring back to FIG. 14, in some embodiments, display software programmed to allow an operator to navigate through image data in multiple directions is configured to prevent an operator from viewing the image data outside angles from which projection data was obtained. For example, the display software may prevent an operator from viewing data from angles outside boundaries 1450$a$ and 1450$a'$, to prevent displaying significant amounts of data that is artificial and potentially misleading to the operator, for example, a radiologist performing a diagnosis on the image.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed function. The one or more controller can be implemented in numerous ways, such as with dedicated hardware, or with general purpose hardware (e.g., one or more processor) that is programmed using microcode or software to perform the functions recited above.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code.

In this respect, it should be appreciated that one embodiment of the invention is directed to a computer readable medium (or multiple computer readable media) (e.g., a computer memory, one or more floppy discs, compact discs, optical discs, magnetic tapes, etc.) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

It should be understood that the term "program" is used herein in a generic sense to refer to any type of computer code or set of instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. The invention is capable of other embodiments and of being practiced or of being carried out in various ways. In particular, the various concepts related to variable radiation energy and variable radiation intensity may be used in any way, either alone or in any combination, as the aspects of the invention are not limited to the specific combinations described herein. Accordingly, the foregoing description and drawings are by way of example only.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A method of displaying image data, the method comprising:
    obtaining projection data of an object using an x-ray imaging device by exposing an object to radiation at a plurality of view angles and detecting at least some of the radiation exiting the object to form the projection data;
    operating a computer to reconstruct the projection data at a reconstruction resolution to form image data comprising a plurality of voxels representing locations within the object, each of the plurality of voxels being assigned an associated intensity indicative of a density of the subject matter at the respective location, the reconstruction resolution defining the resolution of the image data for at least one dimension;

determining a maximum resolution, for the at least one dimension above which variation in intensity between adjacent voxels in the at least one dimension is not supported by information in the projection data, the maximum resolution for the at least one dimension being determined based, at least in part, on at least one of geometry of the x-ray imaging device, a number of the plurality of view angles from which the projection data was obtained, a distribution of the plurality of view angles from which the projection data was obtained, and one or more radiation parameters of the radiation emitted from the x-ray imaging device; and displaying the image data, wherein the image data along the at least one dimension is displayed at or below the maximum resolution.

2. The method of claim 1, wherein determining the maximum resolution includes determining the maximum resolution based on the number and distribution of the plurality of view angles from which the image data was obtained.

3. The method of claim 2, wherein operating a computer includes operating a computer to reconstruct the projection data to form a three-dimensional image having asymmetric resolution, wherein the maximum resolution along the at least one dimension is less than a resolution along at least one other dimension of the three-dimensions.

4. The method of claim 1, wherein obtaining projection data includes obtaining projection data by exposing the object to x-ray radiation, from at least one x-ray source, at a plurality of view angles and detecting at least some of the radiation exiting the object to form the projection data, the projection data indicative of the amount of x-ray radiation absorbed by the object.

5. The method of claim 4, wherein the object is a human female breast, and wherein obtaining projection data includes obtaining projection data by exposing the female human breast to x-ray radiation from a plurality of view angles number less than 30.

6. A method of limiting a viewing angle at which image data may be displayed, the image data reconstructed from projection data obtained by exposing an object to radiation from a plurality of view angles spanning a range having a first angle boundary and a second angle boundary, the method comprising computer implemented acts of:

receiving an indicator from an operator to view the image data from a first angle;

displaying the image data on a display from the first angle if the first angle is within the range bounded by the first angle boundary and the second angle boundary; and preventing the image data from being displayed on the display at the first angle if the first angle is outside of the range bounded by the first angle boundary and the second angle boundary.

* * * * *

UNITED STATES PATENT AND TRADEMARK OFFICE
CERTIFICATE OF CORRECTION

| | | |
|---|---|---|
| PATENT NO. | : 8,238,649 B2 | Page 1 of 1 |
| APPLICATION NO. | : 12/842480 | |
| DATED | : August 7, 2012 | |
| INVENTOR(S) | : Martin Stanton et al. | |

It is certified that error appears in the above-identified patent and that said Letters Patent is hereby corrected as shown below:

At column 19, claim 1, line 5, please change "determining a maximum resolution, for the at least one" to -- determining a maximum resolution for the at least one --.

Signed and Sealed this
Twenty-fifth Day of September, 2012

David J. Kappos
*Director of the United States Patent and Trademark Office*